US008017751B2

(12) United States Patent
Adler

(10) Patent No.: US 8,017,751 B2
(45) Date of Patent: Sep. 13, 2011

(54) HT2R54 RECEPTOR POLYPEPTIDES AND NUCLEIC ACID SEQUENCES

(75) Inventor: Jon Elliot Adler, San Diego, CA (US)

(73) Assignee: Senomyx, Inc., San Diego, CA (US)

( * ) Notice: Subject to any disclaimer, the term of this patent is extended or adjusted under 35 U.S.C. 154(b) by 148 days.

(21) Appl. No.: 12/133,155

(22) Filed: Jun. 4, 2008

(65) Prior Publication Data

US 2009/0017537 A1     Jan. 15, 2009

Related U.S. Application Data

(60) Continuation of application No. 10/724,209, filed on Dec. 1, 2003, now Pat. No. 7,393,654, which is a division of application No. 09/825,882, filed on Apr. 5, 2001, now Pat. No. 7,105,650.

(60) Provisional application No. 60/195,532, filed on Apr. 7, 2000, provisional application No. 60/247,014, filed on Nov. 13, 2000.

(51) Int. Cl.
*C12N 15/12* (2006.01)
*C07K 14/705* (2006.01)

(52) U.S. Cl. .................. 536/23.5; 435/252.3; 435/320.1

(58) Field of Classification Search ......................... None
See application file for complete search history.

(56) References Cited

FOREIGN PATENT DOCUMENTS

WO     99/42470     8/1999

OTHER PUBLICATIONS

Perruccio, et al., "Possible Role for gustducin in Taste Transduction in Hirudo Medicinalis", Society for Neuroscience Abstracts, vol. 26, No. 1-2, Abstract No. 66315, 2000.
Chandrashekar, et al., Cell 100(703-711), 2000.
Bowie, et al., "Deciphering the Message in Protein in Sequences: Tolerance to Amino Acid Substitutions", Science, vol. 247, pp. 1306-1310, Mar. 16, 1990.
Alexander, et al., "Altering the Antigenicity of proteins", Proc. Natl. Acad. Sci. USA, vol. 89, pp. 3352-3356, Apr. 1992.
Hoon, et al., "Putative Mammalian Taste Receptors; A Class of Taste-Specific GPCRs with Distinct Topographic Selective", Cell, vol. 96, p. 541-551, Feb. 19, 1999.
Linderman, "A Taste for Umami", Nature Neuroscience, 01.3, No. 2, pp. 99-100. Feb. 2000.
Brenner, et al. PNAS 95 (6073-6078), 1998.
Guo, et al., "Protein Tolerance to Random Amino Acid change", PNAS, vol. 101, No. 25, pp. 9205-9210, Jun. 22, 2004.
Horrobin, DF, British Med. Journal, 322 (7280) 239, Jul. 2003.
Lahana, R. Drug Discovery Today, 4 (10) 447-445, 1999.

*Primary Examiner* — John Ulm
(74) *Attorney, Agent, or Firm* — Hunton & Williams LLP

(57) ABSTRACT

Functional assays that detect the effect of a particular compound or compounds on the activation of at least one human T2R polypeptide are provided. These assays include e.g., assays which detect the effect of said compound on intracellular calcium, second messengers such as cAMP, cGMP, current e.g., by use of voltage-clamp or patch-clamp, techniques, fluorescence polarization or FRET assays, and the like. These assays are useful in identifying compounds that putatively elicit or modulate (inhibit or enhance) bitter taste in human subjects, e.g. bitter taste blockers. The effect of identified compounds on taste may be further evaluated in human or animal taste tests.

12 Claims, No Drawings

SEQUENCE LISTING

<160> NUMBER OF SEQ ID NOS: 31

<210> SEQ ID NO 1
<211> LENGTH: 1002
<212> TYPE: DNA
<213> ORGANISM: Homo sapiens

<400> SEQUENCE: 1

```
atgttgactc taactcgcat ccgcactgtg tcctatgaag tcaggagtac atttctgttc    60
atttcagtcc tggagtttgc agtggggttt ctgaccaatg ccttcgtttt cttggtgaat   120
ttttgggatg tagtgaagag gcaggcactg agcaacagtg attgtgtgct gctgtgtctc   180
agcatcagcc ggcttttcct gcatggactg ctgttcctga gtgctatcca gcttacccac   240
ttccagaagt tgagtgaacc actgaaccac agctaccaag ccatcatcat gctatggatg   300
attgcaaacc aagccaacct ctggcttgct gcctgcctca gcctgcttta ctgctccaag   360
ctcatccgtt tctctcacac cttcctgatc tgcttggcaa gctgggtctc caggaagatc   420
tcccagatgc tcctgggtat tattctttgc tcctgcatct gcactgtcct ctgtgtttgg   480
tgcttttta gcagacctca cttcacagtc acaactgtgc tattcatgaa taacaataca   540
aggctcaact ggcagattaa agatctcaat ttatttattt cctttctctt ctgctatctg   600
tggtctgtgc ctccttcct attgtttctg gtttcttctg ggatgctgac tgtctccctg   660
ggaaggcaca tgaggacaat gaaggtctat accagaaact ctcgtgaccc cagcctggag   720
gcccacatta aagccctcaa gtctcttgtc tcctttttct gcttctttgt gatatcatcc   780
tgtgttgcct tcatctctgt gccccactg attctgtggc gcgacaaaat aggggtgatg   840
gtttgtgttg ggataatggc agcttgtccc tctgggcatg cagccatcct gatctcaggc   900
aatgccaagt tgaggagagc tgtgatgacc attctgctct gggctcagag cagcctgaag   960
gtaagagccg accacaaggc agattcccgg acactgtgct ga                    1002
```

<210> SEQ ID NO 2
<211> LENGTH: 333
<212> TYPE: PRT
<213> ORGANISM: Homo sapiens

<400> SEQUENCE: 2

```
Met Leu Thr Leu Thr Arg Ile Arg Thr Val Ser Tyr Glu Val Arg Ser
  1               5                  10                  15

Thr Phe Leu Phe Ile Ser Val Leu Glu Phe Ala Val Gly Phe Leu Thr
             20                  25                  30

Asn Ala Phe Val Phe Leu Val Asn Phe Trp Asp Val Val Lys Arg Gln
         35                  40                  45

Ala Leu Ser Asn Ser Asp Cys Val Leu Leu Cys Leu Ser Ile Ser Arg
     50                  55                  60
```

```
Leu Phe Leu His Gly Leu Phe Leu Ser Ala Ile Gln Leu Thr His
 65                  70                  75                  80

Phe Gln Lys Leu Ser Glu Pro Leu Asn His Ser Tyr Gln Ala Ile Ile
             85                  90                  95

Met Leu Trp Met Ile Ala Asn Gln Ala Asn Leu Trp Leu Ala Ala Cys
        100                 105                 110

Leu Ser Leu Leu Tyr Cys Ser Lys Leu Ile Arg Phe Ser His Thr Phe
            115                 120                 125

Leu Ile Cys Leu Ala Ser Trp Val Ser Arg Lys Ile Ser Gln Met Leu
130                 135                 140

Leu Gly Ile Ile Leu Cys Ser Cys Ile Cys Thr Val Leu Cys Val Trp
145                 150                 155                 160

Cys Phe Phe Ser Arg Pro His Phe Thr Val Thr Val Leu Phe Met
                165                 170                 175

Asn Asn Asn Thr Arg Leu Asn Trp Gln Ile Lys Asp Leu Asn Leu Phe
            180                 185                 190

Tyr Ser Phe Leu Phe Cys Tyr Leu Trp Ser Val Pro Pro Phe Leu Leu
            195                 200                 205

Phe Leu Val Ser Ser Gly Met Leu Thr Val Ser Leu Gly Arg His Met
210                 215                 220

Arg Thr Met Lys Val Tyr Thr Arg Asn Ser Arg Asp Pro Ser Leu Glu
225                 230                 235                 240

Ala His Ile Lys Ala Leu Lys Ser Leu Val Ser Phe Phe Cys Phe Phe
            245                 250                 255

Val Ile Ser Ser Cys Val Ala Phe Ile Ser Val Pro Leu Leu Ile Leu
            260                 265                 270

Trp Arg Asp Lys Ile Gly Val Met Val Cys Val Gly Ile Met Ala Ala
            275                 280                 285

Cys Pro Ser Gly His Ala Ala Ile Leu Ile Ser Gly Asn Ala Lys Leu
            290                 295                 300

Arg Arg Ala Val Met Thr Ile Leu Leu Trp Ala Gln Ser Ser Leu Lys
305                 310                 315                 320

Val Arg Ala Asp His Lys Ala Asp Ser Arg Thr Leu Cys
                325                 330

<210> SEQ ID NO 3
<211> LENGTH: 966
<212> TYPE: DNA
<213> ORGANISM: Homo sapiens

<400> SEQUENCE: 3
atgactaaac tctgcgatcc tgcagaaagt gaattgtcgc catttctcat caccttaatt      60
ttagcagttt tacttgctga atacctcatt ggtatcattg caaatggttt catcatggct     120
atacatgcag ctgaatgggt tcaaaataag gcagtttcca caagtggcag atcctggtt     180 ttcctgagtg tatccagaat agctctccaa agcctcatga tgttagaaat taccatcagc     240
tcaacctccc taagttttta ttctgaagac gctgtatatt atgcattcaa ataagttttt     300
atattcttaa attttttgtag cctgtggttt gctgcctggc tcagtttctt ctactttgtg     360
aagattgcca atttctccta ccccctttc ctcaaactga ggtggagaat tactggattg     420 atacccctggc ttctgtggct gtccgtgttt atttccttca gtcacagcat gttctgcatc     480
aacatctgca ctgtgtattg taacaattct ttccctatcc actcctccaa ctccactaag     540
aaaacatact tgtctgagat caatgtggtc ggtctggctt tttcttttaa cctggggatt     600
```

-continued

```
gtgactcctc tgatcatgtt catcctgaca gccaccctgc tgatcctctc tctcaagaga    660
cacaccctac acatgggaag caatgccaca gggtccaacg accccagcat ggaggctcac    720
atgggggcca tcaaagctat cagctacttt ctcattctct acattttcaa tgcagttgct    780
ctgtttatct acctgtccaa catgtttgac atcaacagtc tgtggaataa tttgtgccag    840
atcatcatgg ctgcctaccc tgccagccac tcaattctac tgattcaaga taaccctggg    900
ctgagaagag cctggaagcg gcttcagctt cgacttcatc tttacccaaa agagtggact    960
ctgtga                                                               966
```

```
<210> SEQ ID NO 4
<211> LENGTH: 321
<212> TYPE: PRT
<213> ORGANISM: Homo sapiens

<400> SEQUENCE: 4
```

Met Thr Lys Leu Cys Asp Pro Ala Glu Ser Glu Leu Ser Pro Phe Leu
 1               5                  10                  15

Ile Thr Leu Ile Leu Ala Val Leu Leu Ala Glu Tyr Leu Ile Gly Ile
                20                  25                  30

Ile Ala Asn Gly Phe Ile Met Ala Ile His Ala Ala Glu Trp Val Gln
            35                  40                  45

Asn Lys Ala Val Ser Thr Ser Gly Arg Ile Leu Val Phe Leu Ser Val
        50                  55                  60

Ser Arg Ile Ala Leu Gln Ser Leu Met Met Leu Glu Ile Thr Ile Ser
    65                  70                  75                  80

Ser Thr Ser Leu Ser Phe Tyr Ser Glu Asp Ala Val Tyr Tyr Ala Phe
                85                  90                  95

Lys Ile Ser Phe Ile Phe Leu Asn Phe Cys Ser Leu Trp Phe Ala Ala
            100                 105                 110

Trp Leu Ser Phe Phe Tyr Phe Val Lys Ile Ala Asn Phe Ser Tyr Pro
        115                 120                 125

Leu Phe Leu Lys Leu Arg Trp Arg Ile Thr Gly Leu Ile Pro Trp Leu
    130                 135                 140

Leu Trp Leu Ser Val Phe Ile Ser Phe Ser His Ser Met Phe Cys Ile
145                 150                 155                 160

Asn Ile Cys Thr Val Tyr Cys Asn Asn Ser Phe Pro Ile His Ser Ser
                165                 170                 175

Asn Ser Thr Lys Lys Thr Tyr Leu Ser Glu Ile Asn Val Val Gly Leu
            180                 185                 190

Ala Phe Phe Phe Asn Leu Gly Ile Val Thr Pro Leu Ile Met Phe Ile
        195                 200                 205

Leu Thr Ala Thr Leu Leu Ile Leu Ser Leu Lys Arg His Thr Leu His
    210                 215                 220

Met Gly Ser Asn Ala Thr Gly Ser Asn Asp Pro Ser Met Glu Ala His
225                 230                 235                 240

Met Gly Ala Ile Lys Ala Ile Ser Tyr Phe Leu Ile Leu Tyr Ile Phe
                245                 250                 255

Asn Ala Val Ala Leu Phe Ile Tyr Leu Ser Asn Met Phe Asp Ile Asn
            260                 265                 270

Ser Leu Trp Asn Asn Leu Cys Gln Ile Ile Met Ala Ala Tyr Pro Ala
        275                 280                 285

Ser His Ser Ile Leu Leu Ile Gln Asp Asn Pro Gly Leu Arg Arg Ala
    290                 295                 300

Trp Lys Arg Leu Gln Leu Arg Leu His Leu Tyr Pro Lys Glu Trp Thr

```
                305                 310                 315                 320
Leu

<210> SEQ ID NO 5
<211> LENGTH: 972
<212> TYPE: DNA
<213> ORGANISM: Homo sapiens

<400> SEQUENCE: 5
atggcaacgg tgaacacaga tgccacagat aaagacatat ccaagttcaa ggtcaccttc     60
actttggtgg tctccggaat agagtgcatc actggcatcc ttgggagtgg cttcatcacg    120
gccatctatg gggctgagtg ggccaggggc aaaacactcc ccactggtga ccgcattatg    180
ttgatgctga gcttttccag gctcttgcta cagatttgga tgatgctgga gaacattttc    240
agtctgctat tccgaattgt ttataaccaa aactcagtgt atatcctctt caaagtcatc    300
actgtctttc tgaaccattc caatctctgg tttgctgcct ggctcaaagt cttctattgt    360
cttagaattg caaacttcaa tcatcctttg ttcttcctga tgaagaggaa aatcatagtg    420
ctgatgcctt ggcttctcag gctgtcagtg ttggtttcct taagcttcag ctttcctctc    480
tcgagagatg tcttcaatgt gtatgtgaat agctccattc ctatcccctc ctccaactcc    540
acggagaaga agtacttctc tgagaccaat atggtcaacc tggtattttt ctataacatg    600
gggatcttcg ttcctctgat catgttcatc ctggcagcca ccctgctgat cctctctctc    660
aagagacaca ccctacacat gggaagcaat gccacagggt ccaggacccc cagcatgaag    720
gctcacatag gggccatcaa agccaccagc tactttctca tcctctacat tttcaatgca    780
attgctctat tcttccac gtccaacatc tttgacactt acagttcctg gaatattttg    840
tgcaagatca tcatggctgc ctaccctgcc ggccactcag tacaactgat cttgggcaac    900
cctgggctga aagagcctg gaagcggttt cagcaccaag ttcctctttta cctaaaaggg    960
cagactctgt ga                                                       972

<210> SEQ ID NO 6
<211> LENGTH: 323
<212> TYPE: PRT
<213> ORGANISM: Homo sapiens

<400> SEQUENCE: 6

Met Ala Thr Val Asn Thr Asp Ala Thr Asp Lys Asp Ile Ser Lys Phe
  1               5                  10                  15

Lys Val Thr Phe Thr Leu Val Val Ser Gly Ile Glu Cys Ile Thr Gly
                 20                  25                  30

Ile Leu Gly Ser Gly Phe Ile Thr Ala Ile Tyr Gly Ala Glu Trp Ala
         35                  40                  45

Arg Gly Lys Thr Leu Pro Thr Gly Asp Arg Ile Met Leu Met Leu Ser
     50                  55                  60

Phe Ser Arg Leu Leu Leu Gln Ile Trp Met Met Leu Glu Asn Ile Phe
 65                  70                  75                  80

Ser Leu Leu Phe Arg Ile Val Tyr Asn Gln Asn Ser Val Tyr Ile Leu
                 85                  90                  95

Phe Lys Val Ile Thr Val Phe Leu Asn His Ser Asn Leu Trp Phe Ala
                100                 105                 110

Ala Trp Leu Lys Val Phe Tyr Cys Leu Arg Ile Ala Asn Phe Asn His
            115                 120                 125

Pro Leu Phe Phe Leu Met Lys Arg Lys Ile Ile Val Leu Met Pro Trp
        130                 135                 140
```

```
Leu Leu Arg Leu Ser Val Leu Val Ser Leu Ser Phe Ser Phe Pro Leu
145                 150                 155                 160

Ser Arg Asp Val Phe Asn Val Tyr Val Asn Ser Ser Ile Pro Ile Pro
                165                 170                 175

Ser Ser Asn Ser Thr Glu Lys Lys Tyr Phe Ser Glu Thr Asn Met Val
            180                 185                 190

Asn Leu Val Phe Phe Tyr Asn Met Gly Ile Phe Val Pro Leu Ile Met
        195                 200                 205

Phe Ile Leu Ala Ala Thr Leu Leu Ile Leu Ser Leu Lys Arg His Thr
    210                 215                 220

Leu His Met Gly Ser Asn Ala Thr Gly Ser Arg Asp Pro Ser Met Lys
225                 230                 235                 240

Ala His Ile Gly Ala Ile Lys Ala Thr Ser Tyr Phe Leu Ile Leu Tyr
                245                 250                 255

Ile Phe Asn Ala Ile Ala Leu Phe Leu Ser Thr Ser Asn Ile Phe Asp
                260                 265                 270

Thr Tyr Ser Ser Trp Asn Ile Leu Cys Lys Ile Ile Met Ala Ala Tyr
            275                 280                 285

Pro Ala Gly His Ser Val Gln Leu Ile Leu Gly Asn Pro Gly Leu Arg
        290                 295                 300

Arg Ala Trp Lys Arg Phe Gln His Gln Val Pro Leu Tyr Leu Lys Gly
305                 310                 315                 320

Gln Thr Leu

<210> SEQ ID NO 7
<211> LENGTH: 930
<212> TYPE: DNA
<213> ORGANISM: Homo sapiens

<400> SEQUENCE: 7
atgataactt ttctacccat cattttttcc agtctggtag tggttacatt tgttattgga      60
aattttgcta atggcttcat agcactggta aattccattg agtggttcaa gagacaaaag     120
atctcctttg ctgaccaaat tctcactgct ctggcggtct ccagagttgg tttgctctgg     180
gtattattat taaactggta ttcaactgtg ttgaatccag cttttaatag tgtagaagta     240
agaactactg cttataatat ctgggcagtg atcaaccatt tcagcaactg gcttgctact     300 acccctcagca tattttattt gctcaagatt gccaatttct ccaactttat ttttcttcac    360
ttaaagagga gagttaagag tgtcattctg gtgatgttgt tggggccttt gctattttg      420 gcttgtcatc tttttgtgat aaacatgaat gagattgtgc ggacaaaaga atttgaagga    480
aacatgactt ggaagatcaa attgaagagt gcaatgtact tttcaaatat gactgtaacc    540
atggtagcaa acttagtacc cttcactctg accctactat cttttatgct gttaatctgt    600
tctttgtgta acatctcaa gaagatgcag ctccatggta aaggatctca agatcccagc     660
accaaggtcc acataaaagc tttgcaaact gtgatctcct tcctcttgtt atgtgccatt    720
tactttctgt ccataatgat atcagttttgg agttttggaa gtctggaaaa caaacctgtc   780
ttcatgttct gcaaagctat tagattcagc tatccttcaa tccacccatt catcctgatt    840
tggggaaaca gaagctaaa gcagactttt ctttcagttt tttggcaaat gaggtactgg     900
gtgaaaggag agaagacttc atctccatag                                     930

<210> SEQ ID NO 8
<211> LENGTH: 309
<212> TYPE: PRT
```

<213> ORGANISM: Homo sapiens

<400> SEQUENCE: 8

```
Met Ile Thr Phe Leu Pro Ile Ile Phe Ser Ser Leu Val Val Thr
  1               5                  10                  15

Phe Val Ile Gly Asn Phe Ala Asn Gly Phe Ile Ala Leu Val Asn Ser
                 20                  25                  30

Ile Glu Trp Phe Lys Arg Gln Lys Ile Ser Phe Ala Asp Gln Ile Leu
             35                  40                  45

Thr Ala Leu Ala Val Ser Arg Val Gly Leu Leu Trp Val Leu Leu Leu
         50                  55                  60

Asn Trp Tyr Ser Thr Val Leu Asn Pro Ala Phe Asn Ser Val Glu Val
 65                  70                  75                  80

Arg Thr Thr Ala Tyr Asn Ile Trp Ala Val Ile Asn His Phe Ser Asn
                 85                  90                  95

Trp Leu Ala Thr Thr Leu Ser Ile Phe Tyr Leu Leu Lys Ile Ala Asn
            100                 105                 110

Phe Ser Asn Phe Ile Phe Leu His Leu Lys Arg Arg Val Lys Ser Val
        115                 120                 125

Ile Leu Val Met Leu Leu Gly Pro Leu Leu Phe Leu Ala Cys His Leu
130                 135                 140

Phe Val Ile Asn Met Asn Glu Ile Val Arg Thr Lys Glu Phe Glu Gly
145                 150                 155                 160

Asn Met Thr Trp Lys Ile Lys Leu Lys Ser Ala Met Tyr Phe Ser Asn
                165                 170                 175

Met Thr Val Thr Met Val Ala Asn Leu Val Pro Phe Thr Leu Thr Leu
            180                 185                 190

Leu Ser Phe Met Leu Leu Ile Cys Ser Leu Cys Lys His Leu Lys Lys
        195                 200                 205

Met Gln Leu His Gly Lys Gly Ser Gln Asp Pro Ser Thr Lys Val His
    210                 215                 220

Ile Lys Ala Leu Gln Thr Val Ile Ser Phe Leu Leu Leu Cys Ala Ile
225                 230                 235                 240

Tyr Phe Leu Ser Ile Met Ile Ser Val Trp Ser Phe Gly Ser Leu Glu
                245                 250                 255

Asn Lys Pro Val Phe Met Phe Cys Lys Ala Ile Arg Phe Ser Tyr Pro
            260                 265                 270

Ser Ile His Pro Phe Ile Leu Ile Trp Gly Asn Lys Lys Leu Lys Gln
        275                 280                 285

Thr Phe Leu Ser Val Phe Trp Gln Met Arg Tyr Trp Val Lys Gly Glu
    290                 295                 300

Lys Thr Ser Ser Pro
305
```

<210> SEQ ID NO 9
<211> LENGTH: 930
<212> TYPE: DNA
<213> ORGANISM: Homo sapiens

<400> SEQUENCE: 9

| atgatgagtt ttctacacat tgttttttcc attctagtag tggttgcatt tattccttgga | 60 |
| aattttgcca atggctttat agcactgata aatttcattg cctgggtcaa gagacaaaag | 120 |
| atctcctcag ctgatcaaat tattgctgct ctggcagtct ccagagttgg tttgctctgg | 180 |
| gtaatattat tacattggta ttcaactgtg ttgaatccaa cttcatctaa tttaaaagta | 240 |

```
ataatttta tttctaatgc ctgggcagta accaatcatt tcagcatctg gcttgctact       300
agcctcagca tattttattt gctcaagatc gtcaatttct ccagacttat ttttcatcac       360
ttaaaaagga aggctaagag tgtagttctg gtgatagtgt tggggtcttt gttctttttg       420
gtttgtcacc ttgtgatgaa acacacgtat ataaatgtgt ggacagaaga atgtgaagga       480
aacgtaactt ggaagatcaa actgaggaat gcaatgcacc tttccaactt gactgtagcc       540
atgctagcaa acttgatacc attcactctg accctgatat cttttctgct gttaatctac       600
tctctgtgta acatctgaa gaagatgcag ctccatggca aaggatctca agatcccagc       660
accaagatcc acataaaagc tctgcaaact gtgacctcct tcctcatatt acttgccatt       720
tactttctgt gtctaatcat atcgttttgg aattttaaga tgcgaccaaa agaaattgtc       780
ttaatgcttt gccaagcttt tggaatcata tatccatcat tccactcatt cattctgatt       840
tgggggaaca agacgctaaa gcagaccttt cttttcagttt tgtggcaggt gacttgctgg       900
gcaaaaggac agaaccagtc aactccatag                                       930

<210> SEQ ID NO 10
<211> LENGTH: 309
<212> TYPE: PRT
<213> ORGANISM: Homo sapiens

<400> SEQUENCE: 10

Met Met Ser Phe Leu His Ile Val Phe Ser Ile Leu Val Val Val Ala
 1               5                  10                  15

Phe Ile Leu Gly Asn Phe Ala Asn Gly Phe Ile Ala Leu Ile Asn Phe
                20                  25                  30

Ile Ala Trp Val Lys Arg Gln Lys Ile Ser Ser Ala Asp Gln Ile Ile
            35                  40                  45

Ala Ala Leu Ala Val Ser Arg Val Gly Leu Leu Trp Val Ile Leu Leu
        50                  55                  60

His Trp Tyr Ser Thr Val Leu Asn Pro Thr Ser Ser Asn Leu Lys Val
 65                  70                  75                  80

Ile Ile Phe Ile Ser Asn Ala Trp Ala Val Thr Asn His Phe Ser Ile
                85                  90                  95

Trp Leu Ala Thr Ser Leu Ser Ile Phe Tyr Leu Leu Lys Ile Val Asn
            100                 105                 110

Phe Ser Arg Leu Ile Phe His His Leu Lys Arg Lys Ala Lys Ser Val
        115                 120                 125

Val Leu Val Ile Val Leu Gly Ser Leu Phe Phe Leu Val Cys His Leu
    130                 135                 140

Val Met Lys His Thr Tyr Ile Asn Val Trp Thr Glu Glu Cys Glu Gly
145                 150                 155                 160

Asn Val Thr Trp Lys Ile Lys Leu Arg Asn Ala Met His Leu Ser Asn
                165                 170                 175

Leu Thr Val Ala Met Leu Ala Asn Leu Ile Pro Phe Thr Leu Thr Leu
            180                 185                 190

Ile Ser Phe Leu Leu Leu Ile Tyr Ser Leu Cys Lys His Leu Lys Lys
        195                 200                 205

Met Gln Leu His Gly Lys Gly Ser Gln Asp Pro Ser Thr Lys Ile His
    210                 215                 220

Ile Lys Ala Leu Gln Thr Val Thr Ser Phe Leu Ile Leu Ala Ile
225                 230                 235                 240

Tyr Phe Leu Cys Leu Ile Ile Ser Phe Trp Asn Phe Lys Met Arg Pro
                245                 250                 255
```

```
Lys Glu Ile Val Leu Met Leu Cys Gln Ala Phe Gly Ile Ile Tyr Pro
                260                 265                 270
Ser Phe His Ser Phe Ile Leu Ile Trp Gly Asn Lys Thr Leu Lys Gln
            275                 280                 285
Thr Phe Leu Ser Val Leu Trp Gln Val Thr Cys Trp Ala Lys Gly Gln
        290                 295                 300
Asn Gln Ser Thr Pro
305

<210> SEQ ID NO 11
<211> LENGTH: 930
<212> TYPE: DNA
<213> ORGANISM: Homo sapiens

<400> SEQUENCE: 11
atgacaactt ttatacccat cattttttcc agtgtggtag tggttctatt tgttattgga      60
aattttgcta atggcttcat agcattggta aattccattg agcgggtcaa gagacaaaag     120
atctcttttg ctgaccagat tctcactgct ctggcggtct ccagagttgg tttgctctgg     180
gtattattat taaattggta ttcaactgtg tttaatccag cttttttatag tgtagaagta     240 agaactactg cttataatgt ctgggcagta accggccatt tcagcaactg gcttgctact     300
agcctcagca tatttttattt gctcaagatt gccaatttct ccaaccttat ttttcttcac     360
ttaaagagga gagttaagag tgtcattctg gtgatgctgt ggggcctttt actattttg      420 gcttgtcaac ttttttgtgat aaacatgaaa gagattgtac ggacaaaaga atatgaagga     480
aacttgactt ggaagatcaa attgaggagt gcagtgtacc tttcagatgc gactgtaacc     540
acgctaggaa acttagtgcc cttcactctg accctgctat gttttttgct gttaatctgt     600
tctctgtgta acatctcaa gaagatgcag ctccatggta aaggatctca agatcccagc      660
accaaggtcc acataaaagc tttgcaaact gtgatctttt tcctcttgtt atgtgccgtt     720
tactttctgt ccataatgat atcagtttgg agttttggga gtctggaaaa caaacctgtc     780
ttcatgttct gcaaagctat tagattcagc tatccttcaa tccacccatt catcctgatt     840
tggggaaaca gaagctaaa gcagactttt ctttcagttt gcggcaagt gaggtactgg       900 gtgaaaggag agaagccttc atctccatag                                      930

<210> SEQ ID NO 12
<211> LENGTH: 309
<212> TYPE: PRT
<213> ORGANISM: Homo sapiens

<400> SEQUENCE: 12

Met Thr Thr Phe Ile Pro Ile Ile Phe Ser Ser Val Val Val Leu
  1               5                  10                  15

Phe Val Ile Gly Asn Phe Ala Asn Gly Phe Ile Ala Leu Val Asn Ser
                 20                  25                  30

Ile Glu Arg Val Lys Arg Gln Lys Ile Ser Phe Ala Asp Gln Ile Leu
             35                  40                  45

Thr Ala Leu Ala Val Ser Arg Val Gly Leu Leu Trp Val Leu Leu Leu
         50                  55                  60

Asn Trp Tyr Ser Thr Val Phe Asn Pro Ala Phe Tyr Ser Val Glu Val
 65                  70                  75                  80

Arg Thr Thr Ala Tyr Asn Val Trp Ala Val Thr Gly His Phe Ser Asn
                 85                  90                  95

Trp Leu Ala Thr Ser Leu Ser Ile Phe Tyr Leu Leu Lys Ile Ala Asn
                100                 105                 110
```

```
Phe Ser Asn Leu Ile Phe Leu His Leu Lys Arg Arg Val Lys Ser Val
            115                 120                 125

Ile Leu Val Met Leu Leu Gly Pro Leu Leu Phe Leu Ala Cys Gln Leu
130                 135                 140

Phe Val Ile Asn Met Lys Glu Ile Val Arg Thr Lys Glu Tyr Glu Gly
145                 150                 155                 160

Asn Leu Thr Trp Lys Ile Lys Leu Arg Ser Ala Val Tyr Leu Ser Asp
                165                 170                 175

Ala Thr Val Thr Thr Leu Gly Asn Leu Val Pro Phe Thr Leu Thr Leu
                180                 185                 190

Leu Cys Phe Leu Leu Leu Ile Cys Ser Leu Cys Lys His Leu Lys Lys
            195                 200                 205

Met Gln Leu His Gly Lys Gly Ser Gln Asp Pro Ser Thr Lys Val His
            210                 215                 220

Ile Lys Ala Leu Gln Thr Val Ile Phe Phe Leu Leu Leu Cys Ala Val
225                 230                 235                 240

Tyr Phe Leu Ser Ile Met Ile Ser Val Trp Ser Phe Gly Ser Leu Glu
                245                 250                 255

Asn Lys Pro Val Phe Met Phe Cys Lys Ala Ile Arg Phe Ser Tyr Pro
            260                 265                 270

Ser Ile His Pro Phe Ile Leu Ile Trp Gly Asn Lys Lys Leu Lys Gln
            275                 280                 285

Thr Phe Leu Ser Val Leu Arg Gln Val Arg Tyr Trp Val Lys Gly Glu
            290                 295                 300

Lys Pro Ser Ser Pro
305

<210> SEQ ID NO 13
<211> LENGTH: 900
<212> TYPE: DNA
<213> ORGANISM: Homo sapiens

<400> SEQUENCE: 13
atgatgtgtt ttctgctcat catttcatca attctggtag tgtttgcatt tgttcttgga    60
aatgttgcca atggcttcat agccctagta aatgtcattg actgggttaa cacacgaaag   120
atctcctcag ctgagcaaat tctcactgct ctggtggtct ccagaattgg tttactctgg   180
gtcatgttat tcctttggta tgcaactgtg tttaattctg ctttatatgg tttagaagta   240
agaattgttg cttctaatgc ctgggctgta acgaaccatt tcagcatgtg gcttgctgct   300
agcctcagca tattttgttt gctcaagatt gccaatttct ccaaccttat ttctctccac   360
ctaaagaaga gaattaagag tgttgttctg gtgatactgt ggggcccttg gtatttctg    420 atttgtaatc ttgctgtgat aaccatggat gagagagtgt ggacaaaaga atatgaagga   480
aatgtgactt ggaagatcaa attgaggaat gcaatacacc tttcaagctt gactgtaact   540
actctagcaa acctcatacc ctttactctg agcctaatat gttttctgct gttaatctgt   600
tctctttgta acatctcaa gaagatgcgg ctccatagca aggatctca agatcccagc    660 accaaggtcc atataaaagc tttgcaaact gtgaccctcc tcctcatgtt atttgccatt   720
tactttctgt gtataatcac atcaacttgg aatcttagga cacagcagag caaacttgta   780
ctcctgcttt gccaaactgt tgcaatcatg tatccttcat tccactcatt catcctgatt   840
atgggaagta ggaagctaaa acagaccttt cttcagtttt gtggcagat gacacgctga    900

<210> SEQ ID NO 14
```

<211> LENGTH: 299
<212> TYPE: PRT
<213> ORGANISM: Homo sapiens

<400> SEQUENCE: 14

```
Met Met Cys Phe Leu Leu Ile Ile Ser Ser Ile Leu Val Val Phe Ala
 1               5                  10                  15

Phe Val Leu Gly Asn Val Ala Asn Gly Phe Ile Ala Leu Val Asn Val
            20                  25                  30

Ile Asp Trp Val Asn Thr Arg Lys Ile Ser Ser Ala Glu Gln Ile Leu
        35                  40                  45

Thr Ala Leu Val Val Ser Arg Ile Gly Leu Leu Trp Val Met Leu Phe
 50                  55                  60

Leu Trp Tyr Ala Thr Val Phe Asn Ser Ala Leu Tyr Gly Leu Glu Val
 65                  70                  75                  80

Arg Ile Val Ala Ser Asn Ala Trp Ala Val Thr Asn His Phe Ser Met
                85                  90                  95

Trp Leu Ala Ala Ser Leu Ser Ile Phe Cys Leu Leu Lys Ile Ala Asn
            100                 105                 110

Phe Ser Asn Leu Ile Ser Leu His Leu Lys Lys Arg Ile Lys Ser Val
        115                 120                 125

Val Leu Val Ile Leu Leu Gly Pro Leu Val Phe Leu Ile Cys Asn Leu
    130                 135                 140

Ala Val Ile Thr Met Asp Glu Arg Val Trp Thr Lys Glu Tyr Glu Gly
145                 150                 155                 160

Asn Val Thr Trp Lys Ile Lys Leu Arg Asn Ala Ile His Leu Ser Ser
                165                 170                 175

Leu Thr Val Thr Thr Leu Ala Asn Leu Ile Pro Phe Thr Leu Ser Leu
            180                 185                 190

Ile Cys Phe Leu Leu Leu Ile Cys Ser Leu Cys Lys His Leu Lys Lys
        195                 200                 205

Met Arg Leu His Ser Lys Gly Ser Gln Asp Pro Ser Thr Lys Val His
    210                 215                 220

Ile Lys Ala Leu Gln Thr Val Thr Ser Phe Leu Met Leu Phe Ala Ile
225                 230                 235                 240

Tyr Phe Leu Cys Ile Ile Thr Ser Thr Trp Asn Leu Arg Thr Gln Gln
                245                 250                 255

Ser Lys Leu Val Leu Leu Cys Gln Thr Val Ala Ile Met Tyr Pro
            260                 265                 270

Ser Phe His Ser Phe Ile Leu Ile Met Gly Ser Arg Lys Leu Lys Gln
        275                 280                 285

Thr Phe Leu Ser Val Leu Trp Gln Met Thr Arg
    290                 295
```

<210> SEQ ID NO 15
<211> LENGTH: 900
<212> TYPE: DNA
<213> ORGANISM: Homo sapiens

<400> SEQUENCE: 15

| | | | | | | |
|---|---|---|---|---|---|---|
| atgataactt | ttctatacat | ttttttttca | attctaataa | tggtttttatt | tgttctcgga | 60 |
| aactttgcca | atggcttcat | agcactggta | aatttcattg | actgggtgaa | gagaaaaaag | 120 |
| atctcctcag | ctgaccaaat | tctcactgct | ctggcggtct | ccagaattgg | tttgctctgg | 180 |
| gcattattat | taaattggta | tttaactgtg | ttgaatccag | cttttttatag | tgtagaatta | 240 |
| agaattactt | cttataatgc | ctgggttgta | accaaccatt | tcagcatgtg | gcttgctgct | 300 |

```
aacctcagca tatttatttt gctcaagatt gccaatttct ccaaccttct ttttcttcat    360
ttaaagagga gagttaggag tgtcattctg gtgatactgt tggggacttt gatattttg    420 gtttgtcatc ttcttgtggc aaacatggat gagagtatgt gggcagaaga atatgaagga    480
aacatgactg ggaagatgaa attgaggaat acagtacatc tttcatattt gactgtaact    540
accctatgga gcttcatacc ctttactctg tccctgatat cttttctgat gctaatctgt    600
tctctgtgta aacatctcaa gaagatgcag ctccatggag aaggatcgca agatctcagc    660
accaaggtcc acataaaagc tttgcaaact ctgatctcct tcctcttgtt atgtgccatt    720
ttctttctat tcctaatcgt ttcggtttgg agtcctagga ggctgcggaa tgacccggtt    780
gtcatggtta gcaaggctgt tggaaacata tatcttgcat tcgactcatt catcctaatt    840
tggagaacca agaagctaaa acacaccttt cttttgattt tgtgtcagat taggtgctga    900
```

<210> SEQ ID NO 16
<211> LENGTH: 299
<212> TYPE: PRT
<213> ORGANISM: Homo sapiens

<400> SEQUENCE: 16

```
Met Ile Thr Phe Leu Tyr Ile Phe Phe Ser Ile Leu Ile Met Val Leu
 1               5                  10                  15

Phe Val Leu Gly Asn Phe Ala Asn Gly Phe Ile Ala Leu Val Asn Phe
             20                  25                  30

Ile Asp Trp Val Lys Arg Lys Ile Ser Ser Ala Asp Gln Ile Leu
         35                  40                  45

Thr Ala Leu Ala Val Ser Arg Ile Gly Leu Leu Trp Ala Leu Leu Leu
     50                  55                  60

Asn Trp Tyr Leu Thr Val Leu Asn Pro Ala Phe Tyr Ser Val Glu Leu
 65                  70                  75                  80

Arg Ile Thr Ser Tyr Asn Ala Trp Val Val Thr Asn His Phe Ser Met
                 85                  90                  95

Trp Leu Ala Ala Asn Leu Ser Ile Phe Tyr Leu Leu Lys Ile Ala Asn
            100                 105                 110

Phe Ser Asn Leu Leu Phe Leu His Leu Lys Arg Arg Val Arg Ser Val
        115                 120                 125

Ile Leu Val Ile Leu Leu Gly Thr Leu Ile Phe Leu Val Cys His Leu
    130                 135                 140

Leu Val Ala Asn Met Asp Glu Ser Met Trp Ala Glu Glu Tyr Glu Gly
145                 150                 155                 160

Asn Met Thr Gly Lys Met Lys Leu Arg Asn Thr Val His Leu Ser Tyr
                165                 170                 175

Leu Thr Val Thr Thr Leu Trp Ser Phe Ile Pro Phe Thr Leu Ser Leu
            180                 185                 190

Ile Ser Phe Leu Met Leu Ile Cys Ser Leu Cys Lys His Leu Lys Lys
        195                 200                 205

Met Gln Leu His Gly Glu Gly Ser Gln Asp Leu Ser Thr Lys Val His
    210                 215                 220

Ile Lys Ala Leu Gln Thr Leu Ile Ser Phe Leu Leu Leu Cys Ala Ile
225                 230                 235                 240

Phe Phe Leu Phe Leu Ile Val Ser Val Trp Ser Pro Arg Arg Leu Arg
                245                 250                 255

Asn Asp Pro Val Val Met Val Ser Lys Ala Val Gly Asn Ile Tyr Leu
            260                 265                 270
```

Ala Phe Asp Ser Phe Ile Leu Ile Trp Arg Thr Lys Lys Leu Lys His
        275                 280                 285

Thr Phe Leu Leu Ile Leu Cys Gln Ile Arg Cys
        290                 295

<210> SEQ ID NO 17
<211> LENGTH: 924
<212> TYPE: DNA
<213> ORGANISM: Homo sapiens

<400> SEQUENCE: 17

| | | | | | |
|---|---|---|---|---|---|
| atgcaagcag | cactgacggc | cttcttcgtg | ttgctcttta | gcctgctgag | tcttctgggg | 60 |
| attgcagcga | atggcttcat | tgtgctggtg | ctgggcaggg | agtggctgcg | atatggcagg | 120 |
| ttgctgccct | tggatatgat | cctcattagc | ttgggtgcct | cccgcttctg | cctgcagttg | 180 |
| gttgggacgg | tgcacaactt | ctactactct | gcccagaagg | tcgagtactc | tgggggtctc | 240 |
| ggccgacagt | tcttccatct | cacactggac | ttcctgaact | cagccacctt | ctggttttgc | 300 |
| agctggctca | gtgtcctgtt | ctgtgtgaag | attgctaaca | tcacacactc | caccttcctg | 360 |
| tggctgaagt | ggaggttccc | agggtgggtg | ccctggctcc | tgttgggctc | tgtcctgatc | 420 |
| tccttcatca | taaccctgct | gttttttttgg | gtgaactacc | ctgtatatca | agaattttta | 480 |
| attagaaaat | tttctgggaa | catgacctac | aagtggaata | caaggataga | aacatactat | 540 |
| ttcccatccc | tgaaactggt | catctggtca | attcctttt | ctgtttttct | ggtctcaatt | 600 |
| atgctgttaa | ttaattctct | gaggaggcat | actcagagaa | tgcagcacaa | cgggcacagc | 660 |
| ctgcaggacc | ccagcaccca | ggctcacacc | agagctctga | agtccctcat | ctccttcctc | 720 |
| attctttatg | ctctgtcctt | tctgtccctg | atcattgatg | ccgcaaaatt | tatctccatg | 780 |
| cagaacgact | tttactggcc | atggcaaatt | gcagtctacc | tgtgcatatc | tgtccatccc | 840 |
| ttcatcctca | tcttcagcaa | cctcaagctt | cgaagcgtgt | ctcgcagct | cctgttgttg | 900 |
| gcaaggggct | tctgggtggc | ctag | | | | 924 |

<210> SEQ ID NO 18
<211> LENGTH: 307
<212> TYPE: PRT
<213> ORGANISM: Homo sapiens

<400> SEQUENCE: 18

Met Gln Ala Ala Leu Thr Ala Phe Phe Val Leu Leu Phe Ser Leu Leu
  1               5                  10                  15

Ser Leu Leu Gly Ile Ala Ala Asn Gly Phe Ile Val Leu Val Leu Gly
             20                  25                  30

Arg Glu Trp Leu Arg Tyr Gly Arg Leu Leu Pro Leu Asp Met Ile Leu
         35                  40                  45

Ile Ser Leu Gly Ala Ser Arg Phe Cys Leu Gln Leu Gly Thr Val
     50                  55                  60

His Asn Phe Tyr Tyr Ser Ala Gln Lys Val Glu Tyr Ser Gly Gly Leu
 65                  70                  75                  80

Gly Arg Gln Phe Phe His Leu His Leu Asn Ser Ala Thr
                 85                  90                  95

Phe Trp Phe Cys Ser Trp Leu Ser Val Leu Cys Val Lys Ile Ala
                100                 105                 110

Asn Ile Thr His Ser Thr Phe Leu Trp Leu Lys Trp Arg Phe Pro Gly
            115                 120                 125

Trp Val Pro Trp Leu Leu Leu Gly Ser Val Leu Ile Ser Phe Ile Ile
        130                 135                 140

Thr Leu Leu Phe Phe Trp Val Asn Tyr Pro Val Tyr Gln Glu Phe Leu
145                 150                 155                 160

Ile Arg Lys Phe Ser Gly Asn Met Thr Tyr Lys Trp Asn Thr Arg Ile
            165                 170                 175

Glu Thr Tyr Tyr Phe Pro Ser Leu Lys Leu Val Ile Trp Ser Ile Pro
            180                 185                 190

Phe Ser Val Phe Leu Val Ser Ile Met Leu Leu Ile Asn Ser Leu Arg
        195                 200                 205

Arg His Thr Gln Arg Met Gln His Asn Gly His Ser Leu Gln Asp Pro
    210                 215                 220

Ser Thr Gln Ala His Thr Arg Ala Leu Lys Ser Leu Ile Ser Phe Leu
225                 230                 235                 240

Ile Leu Tyr Ala Leu Ser Phe Leu Ser Leu Ile Ile Asp Ala Ala Lys
                245                 250                 255

Phe Ile Ser Met Gln Asn Asp Phe Tyr Trp Pro Trp Gln Ile Ala Val
                260                 265                 270

Tyr Leu Cys Ile Ser Val His Pro Phe Ile Leu Ile Phe Ser Asn Leu
        275                 280                 285

Lys Leu Arg Ser Val Phe Ser Gln Leu Leu Leu Leu Ala Arg Gly Phe
    290                 295                 300

Trp Val Ala
305

<210> SEQ ID NO 19
<211> LENGTH: 930
<212> TYPE: DNA
<213> ORGANISM: Homo sapiens

<400> SEQUENCE: 19

```
atgataactt tctgcccat cattttttcc attctaatag tggttacatt tgtgattgga       60
aattttgcta atggcttcat agcattggta aattccattg agtggttcaa gagacaaaag      120
atctcttttg ctgaccaaat tctcactgct ctggcagtct ccagagttgg tttactctgg      180
gtattagtat taaattggta tgcaactgag ttgaatccag cttttaacag tatagaagta      240
agaattactg cttacaatgt ctgggcagta atcaaccatt tcagcaactg gcttgctact      300
agcctcagca tattttatt gctcaagatt gccaatttct ccaaccttat ttttcttcac       360
ttaaagagga gagttaagag tgttgttctg gtgatactat tggggccttt gctattttg       420
gtttgtcatc tttttgtgat aaacatgaat cagattatat ggacaaaaga atatgaagga     480
aacatgactt ggaagatcaa actgaggagt gcaatgtacc tttcaaatac aacggtaacc     540
atcctagcaa acttagttcc cttcactctg accctgatat cttttctgct gttaatctgt     600
tctctgtgta acatctcaa aaagatgcag ctccatggca aaggatctca agatcccagc      660
atgaaggtcc acataaaagc tttgcaaact gtgacctcct tcctcttgtt atgtgccatt     720
tactttctgt ccataatcat gtcagtttgg agttttgaga gtctggaaaa caaacctgtc     780
ttcatgttct gcgaagctat tgcattcagc tatccttcaa cccacccatt catcctgatt     840
tggggaaaca agaagctaaa gcagactttt ctttcagttt tgtggcatgt gaggtactgg     900
gtgaaaggag agaagccttc atcttcatag                                      930
```

<210> SEQ ID NO 20
<211> LENGTH: 309
<212> TYPE: PRT
<213> ORGANISM: Homo sapiens

```
<400> SEQUENCE: 20

Met Ile Thr Phe Leu Pro Ile Ile Phe Ser Ile Leu Ile Val Val Thr
 1               5                  10                  15

Phe Val Ile Gly Asn Phe Ala Asn Gly Phe Ile Ala Leu Val Asn Ser
                20                  25                  30

Ile Glu Trp Phe Lys Arg Gln Lys Ile Ser Phe Ala Asp Gln Ile Leu
            35                  40                  45

Thr Ala Leu Ala Val Ser Arg Val Gly Leu Leu Trp Val Leu Val Leu
        50                  55                  60

Asn Trp Tyr Ala Thr Glu Leu Asn Pro Ala Phe Asn Ser Ile Glu Val
 65                  70                  75                  80

Arg Ile Thr Ala Tyr Asn Val Trp Ala Val Ile Asn His Phe Ser Asn
                85                  90                  95

Trp Leu Ala Thr Ser Leu Ser Ile Phe Tyr Leu Leu Lys Ile Ala Asn
                100                 105                 110

Phe Ser Asn Leu Ile Phe Leu His Leu Lys Arg Arg Val Lys Ser Val
            115                 120                 125

Val Leu Val Ile Leu Leu Gly Pro Leu Leu Phe Leu Val Cys His Leu
        130                 135                 140

Phe Val Ile Asn Met Asn Gln Ile Ile Trp Thr Lys Glu Tyr Glu Gly
145                 150                 155                 160

Asn Met Thr Trp Lys Ile Lys Leu Arg Ser Ala Met Tyr Leu Ser Asn
                165                 170                 175

Thr Thr Val Thr Ile Leu Ala Asn Leu Val Pro Phe Thr Leu Thr Leu
            180                 185                 190

Ile Ser Phe Leu Leu Leu Ile Cys Ser Leu Cys Lys His Leu Lys Lys
        195                 200                 205

Met Gln Leu His Gly Lys Gly Ser Gln Asp Pro Ser Met Lys Val His
    210                 215                 220

Ile Lys Ala Leu Gln Thr Val Thr Ser Phe Leu Leu Cys Ala Ile
225                 230                 235                 240

Tyr Phe Leu Ser Ile Ile Met Ser Val Trp Ser Phe Glu Ser Leu Glu
                245                 250                 255

Asn Lys Pro Val Phe Met Phe Cys Glu Ala Ile Ala Phe Ser Tyr Pro
            260                 265                 270

Ser Thr His Pro Phe Ile Leu Ile Trp Gly Asn Lys Lys Leu Lys Gln
        275                 280                 285

Thr Phe Leu Ser Val Leu Trp His Val Arg Tyr Trp Val Lys Gly Glu
    290                 295                 300

Lys Pro Ser Ser Ser
305

<210> SEQ ID NO 21
<211> LENGTH: 930
<212> TYPE: DNA
<213> ORGANISM: Homo sapiens

<400> SEQUENCE: 21
atggtatatt ttctgctcat cattttatca attctggtag tgtttgcatt tgttcttgga      60
aattttccca atggcttcat agctctagta aatgtcattg actgggttaa gacacgaaag     120
atctcctcag ctgaccaaat cctcactgct ctggtggtct ccagaattgg tttactctgg     180
gtcatattat tacattggta tgcaaatgtg tttaattcag ctttatatag ttcagaagta     240
ggagctgttg cttctaatat ctcagcaata atcaaccatt tcagcatctg gcttgctgct     300
```

```
agcctcagca tatttattt gctcaagatt gccaatttct ccaaccttat ttttctccac      360
ctaaagaaga gaattaggag tgttgttctg gtgatactgt tgggtccctt ggtatttttg      420
atttgtaatc ttgctgtgat aaccatggat gacagtgtgt ggacaaaaga atatgaagga      480
aatgtgactt ggaagatcaa attgaggaat gcaatacacc tttcaaactt gactgtaagc      540
acactagcaa acctcatacc cttcattctg accctaatat gttttctgct gttaatctgt      600
tctctgcata aacatctcaa gaagatgcag ctccatggca aaggatctca agatctcagc      660
accaaggtcc acataaaagc tttgcaaact gtgatctcct tcctcatgtt atatgccatt      720
tactttctgt atctaatcac attaacctgg aatctttgaa cacagcagaa caaacttgta      780
ttcctgcttt gccaaactct tggaatcatg tatccttcat tccactcatt cttcctgatt      840
atgggaagca ggaaactaaa acagacgttt ctttcagttt tatgtcaggt cacatgctta      900
gtgaaaggac agcaaccctc aactccatag                                      930

<210> SEQ ID NO 22
<211> LENGTH: 885
<212> TYPE: DNA
<213> ORGANISM: Homo sapiens

<400> SEQUENCE: 22
atgatatgtt ttctgctcat cattttatca attctggtag tgtttgcatt tgttcttgga       60
aatgttgcca atggcttcat agctctagta ggtgtccttg agtgggttaa gacacaaaag      120
atctcatcag ctgaccaaat ttctcactgc tctggtggtg tccagagttg gtttactctg      180
ggtcatatta ttacattggt atgcaactgt gtttaatttg gcttcacata gattagaagt      240
aagaattttt ggttctaatg tctcagcaat aaccaagcat ttcagcatct gggtgttact      300
agcctcagca tatttcattt gctcaagact gccaatttct ccaaccttat ttttctccac      360
ctaaagaaaa ggattaagaa tgttggtttg gtgatgctgt tggggcccctt ggtatttttc      420 atttgtaatc ttgctctgat aaccacgggt gagagtgtgt ggacaaaaga atatgaagga      480
aatttgtctt ggatgatcaa attgaggaat gcaatacagc tttcaaactt gactgtaacc      540
atgccagcaa acgtcacacc ctgcactctg acactaatat cttttctgct gttaatctat      600
tctccatgta aacatgtcaa gaagatgcag ctccatggca aaggatctca acatctcagc      660
accaaggtgc acataaaagc tttgcaaact gtgatctcct tccttatgtt atttgccatt      720
tactttctgt gtctaatcac atcaacttgg aatcctagga ctcagcagag caaacttgta      780
ttcctgcttt accaaactct tggattcatg tatcttttgt tccactcatt catcctgact      840
atgggaagta ggaagccaaa acagacctttt cttcagcctt tgtga                    885

<210> SEQ ID NO 23
<211> LENGTH: 912
<212> TYPE: DNA
<213> ORGANISM: Mus sp.

<400> SEQUENCE: 23
atgacctccc ctttcccagc tatttatcac atggtcatca tgacagcaga gtttctcatc       60
gggactacag tgaatggatt ccttatcatt gtgaactgct atgacttgtt caagagccga      120
acgttcctga tcctgcagac cctcttgatg tgcacagggc tgtccagact cggtctgcag      180
ataatgctca tgacccaaag cttcttctct gtgttctttc catactctta tgaggaaaat      240
atttatagtt cagatataat gttcgtctgg atgttcttca gctcgattgg cctctggttt      300
gccacatgtc tctctgtctt ttactgcctc aagatttcag gcttcactcc accctggttt      360
```

-continued

```
ctttggctga aattcagaat ttcaaagctc atattttggc tgcttctggg cagcttgctg    420
gcctctctgg gcactgcaac tgtgtgcatc gaggtaggtt tccctttaat tgaggatggc    480
tatgtcctga aaacgcagg actaaatgat agtaatgcca agctagtgag aaataatgac     540
ttgctcctca tcaacctgat cctcctgctt ccctgtctg tgtttgtgat gtgcacctct     600
atgttatttg tttctcttta caagcacatg cactggatgc aaagcgaatc tcacaagctg    660
tcaagtgcca gaaccgaagc tcatataaat gcattaaaga cagtgacaac attcttttgt    720
ttctttgttt cttactttgc tgccttcatg gcaaatatga catttagaat tccatacaga    780
agtcatcagt tcttcgtggt gaaggaaatc atggcagcat atcccgccgg ccactctgtc    840
ataatcgtct tgagtaactc taagttcaaa gacttattca ggagaatgat ctgtctacag    900
aaggaagagt ga                                                        912
```

<210> SEQ ID NO 24
<211> LENGTH: 303
<212> TYPE: PRT
<213> ORGANISM: Mus sp.

<400> SEQUENCE: 24

```
Met Thr Ser Pro Phe Pro Ala Ile Tyr His Met Val Ile Met Thr Ala
  1               5                  10                  15

Glu Phe Leu Ile Gly Thr Thr Val Asn Gly Phe Leu Ile Val Asn
             20                  25                  30

Cys Tyr Asp Leu Phe Lys Ser Arg Thr Phe Leu Ile Leu Gln Thr Leu
         35                  40                  45

Leu Met Cys Thr Gly Leu Ser Arg Leu Gly Leu Gln Ile Met Leu Met
     50                  55                  60

Thr Gln Ser Phe Phe Ser Val Phe Phe Pro Tyr Ser Tyr Glu Glu Asn
 65                  70                  75                  80

Ile Tyr Ser Ser Asp Ile Met Phe Val Trp Met Phe Ser Ser Ile
                 85                  90                  95

Gly Leu Trp Phe Ala Thr Cys Leu Ser Val Phe Tyr Cys Leu Lys Ile
            100                 105                 110

Ser Gly Phe Thr Pro Pro Trp Phe Leu Trp Leu Lys Phe Arg Ile Ser
        115                 120                 125

Lys Leu Ile Phe Trp Leu Leu Leu Gly Ser Leu Ala Ser Leu Gly
    130                 135                 140

Thr Ala Thr Val Cys Ile Glu Val Gly Phe Pro Leu Ile Glu Asp Gly
145                 150                 155                 160

Tyr Val Leu Arg Asn Ala Gly Leu Asn Asp Ser Asn Ala Lys Leu Val
                165                 170                 175

Arg Asn Asn Asp Leu Leu Leu Ile Asn Leu Ile Leu Leu Pro Leu
            180                 185                 190

Ser Val Phe Val Met Cys Thr Ser Met Leu Phe Val Ser Leu Tyr Lys
        195                 200                 205

His Met His Trp Met Gln Ser Glu Ser His Lys Leu Ser Ser Ala Arg
    210                 215                 220

Thr Glu Ala His Ile Asn Ala Leu Lys Thr Val Thr Thr Phe Phe Cys
225                 230                 235                 240

Phe Phe Val Ser Tyr Phe Ala Ala Phe Met Ala Asn Met Thr Phe Arg
                245                 250                 255

Ile Pro Tyr Arg Ser His Gln Phe Phe Val Val Lys Glu Ile Met Ala
            260                 265                 270

Ala Tyr Pro Ala Gly His Ser Val Ile Ile Val Leu Ser Asn Ser Lys
```

```
                        275                 280                 285
Phe Lys Asp Leu Phe Arg Arg Met Ile Cys Leu Gln Lys Glu Glu
            290                 295                 300

<210> SEQ ID NO 25
<211> LENGTH: 20
<212> TYPE: PRT
<213> ORGANISM: Artificial Sequence
<220> FEATURE:
<221> NAME/KEY: MOD_RES
<222> LOCATION: (2)
<223> OTHER INFORMATION: Phe or Gly
<220> FEATURE:
<221> NAME/KEY: MOD_RES
<222> LOCATION: (3)
<223> OTHER INFORMATION: Ile, Val or Leu
<220> FEATURE:
<221> NAME/KEY: MOD_RES
<222> LOCATION: (4)
<223> OTHER INFORMATION: Val or Leu
<220> FEATURE:
<221> NAME/KEY: MOD_RES
<222> LOCATION: (6)
<223> OTHER INFORMATION: Ile or Val
<220> FEATURE:
<221> NAME/KEY: MOD_RES
<222> LOCATION: (7)
<223> OTHER INFORMATION: Leu or Val
<220> FEATURE:
<221> NAME/KEY: MOD_RES
<222> LOCATION: (10)
<223> OTHER INFORMATION: Gly or Thr
<220> FEATURE:
<221> NAME/KEY: MOD_RES
<222> LOCATION: (13)
<223> OTHER INFORMATION: Val or Ala
<220> FEATURE:
<221> NAME/KEY: MOD_RES
<222> LOCATION: (18)
<223> OTHER INFORMATION: Ile or Met
<220> FEATURE:
<223> OTHER INFORMATION: Description of Artificial Sequence: Consensus
      sequence

<400> SEQUENCE: 25

Glu Xaa Xaa Xaa Gly Xaa Xaa Gly Asn Xaa Phe Ile Xaa Leu Val Asn
1               5                   10                  15

Cys Xaa Asp Trp
            20

<210> SEQ ID NO 26
<211> LENGTH: 14
<212> TYPE: PRT
<213> ORGANISM: Artificial Sequence
<220> FEATURE:
<221> NAME/KEY: MOD_RES
<222> LOCATION: (1)
<223> OTHER INFORMATION: Asp or Gly
<220> FEATURE:
<221> NAME/KEY: MOD_RES
<222> LOCATION: (2)
<223> OTHER INFORMATION: Phe or Leu
<220> FEATURE:
<221> NAME/KEY: MOD_RES
<222> LOCATION: (3)
<223> OTHER INFORMATION: Ile or Leu
<220> FEATURE:
<221> NAME/KEY: MOD_RES
<222> LOCATION: (5)
<223> OTHER INFORMATION: Thr or Ile
<220> FEATURE:
<221> NAME/KEY: MOD_RES
<222> LOCATION: (6)
<223> OTHER INFORMATION: Gly, Ala or Ser
<220> FEATURE:
```

```
<221> NAME/KEY: MOD_RES
<222> LOCATION: (13)
<223> OTHER INFORMATION: Cys, Gly or Phe
<220> FEATURE:
<223> OTHER INFORMATION: Description of Artificial Sequence: Consensus
      sequence

<400> SEQUENCE: 26

Xaa Xaa Xaa Leu Xaa Xaa Leu Ala Ile Ser Arg Ile Xaa Leu
 1               5                  10

<210> SEQ ID NO 27
<211> LENGTH: 13
<212> TYPE: PRT
<213> ORGANISM: Artificial Sequence
<220> FEATURE:
<221> NAME/KEY: MOD_RES
<222> LOCATION: (3)
<223> OTHER INFORMATION: Leu or Phe
<220> FEATURE:
<221> NAME/KEY: MOD_RES
<222> LOCATION: (4)
<223> OTHER INFORMATION: Ser, Thr or Asn
<220> FEATURE:
<221> NAME/KEY: MOD_RES
<222> LOCATION: (5)
<223> OTHER INFORMATION: Leu, Ile or Val
<220> FEATURE:
<221> NAME/KEY: MOD_RES
<222> LOCATION: (7)
<223> OTHER INFORMATION: Phe or Leu
<220> FEATURE:
<221> NAME/KEY: MOD_RES
<222> LOCATION: (8)
<223> OTHER INFORMATION: Ala or Thr
<220> FEATURE:
<221> NAME/KEY: MOD_RES
<222> LOCATION: (10)
<223> OTHER INFORMATION: Cys, Ser or Asn
<220> FEATURE:
<221> NAME/KEY: MOD_RES
<222> LOCATION: (12)
<223> OTHER INFORMATION: Ser, Asn or Gly
<220> FEATURE:
<221> NAME/KEY: MOD_RES
<222> LOCATION: (13)
<223> OTHER INFORMATION: Ile or Val
<220> FEATURE:
<223> OTHER INFORMATION: Description of Artificial Sequence: Consensus
      sequence

<400> SEQUENCE: 27

Asn His Xaa Xaa Xaa Trp Xaa Xaa Thr Xaa Leu Xaa Xaa
 1               5                  10

<210> SEQ ID NO 28
<211> LENGTH: 18
<212> TYPE: PRT
<213> ORGANISM: Artificial Sequence
<220> FEATURE:
<221> NAME/KEY: MOD_RES
<222> LOCATION: (3)
<223> OTHER INFORMATION: Phe or Cys
<220> FEATURE:
<221> NAME/KEY: MOD_RES
<222> LOCATION: (8)
<223> OTHER INFORMATION: Asn or Ser
<220> FEATURE:
<221> NAME/KEY: MOD_RES
<222> LOCATION: (11)
<223> OTHER INFORMATION: His or Asn
<220> FEATURE:
<221> NAME/KEY: MOD_RES
<222> LOCATION: (12)
<223> OTHER INFORMATION: Pro or Ser
<220> FEATURE:
```

```
<221> NAME/KEY: MOD_RES
<222> LOCATION: (13)
<223> OTHER INFORMATION: Leu, Ile or Val
<220> FEATURE:
<221> NAME/KEY: MOD_RES
<222> LOCATION: (16)
<223> OTHER INFORMATION: Trp or Tyr
<220> FEATURE:
<223> OTHER INFORMATION: Description of Artificial Sequence: Consensus
      sequence

<400> SEQUENCE: 28

Phe Tyr Xaa Leu Lys Ile Ala Xaa Phe Ser Xaa Xaa Xaa Phe Leu Xaa
 1               5                  10                  15

Leu Lys

<210> SEQ ID NO 29
<211> LENGTH: 14
<212> TYPE: PRT
<213> ORGANISM: Artificial Sequence
<220> FEATURE:
<221> NAME/KEY: MOD_RES
<222> LOCATION: (4)
<223> OTHER INFORMATION: Ile, Phe or Val
<220> FEATURE:
<221> NAME/KEY: MOD_RES
<222> LOCATION: (8)
<223> OTHER INFORMATION: Lys or Arg
<220> FEATURE:
<221> NAME/KEY: MOD_RES
<222> LOCATION: (10)
<223> OTHER INFORMATION: Ser or Thr
<220> FEATURE:
<221> NAME/KEY: MOD_RES
<222> LOCATION: (11)
<223> OTHER INFORMATION: Lys or Arg
<220> FEATURE:
<221> NAME/KEY: MOD_RES
<222> LOCATION: (12)
<223> OTHER INFORMATION: Gln or Lys
<220> FEATURE:
<221> NAME/KEY: MOD_RES
<222> LOCATION: (13)
<223> OTHER INFORMATION: Met or Ile
<220> FEATURE:
<221> NAME/KEY: MOD_RES
<222> LOCATION: (14)
<223> OTHER INFORMATION: Gln or Lys
<220> FEATURE:
<223> OTHER INFORMATION: Description of Artificial Sequence: Consensus
      sequence

<400> SEQUENCE: 29

Leu Leu Ile Xaa Ser Leu Trp Xaa His Xaa Xaa Xaa Xaa Xaa
 1               5                  10

<210> SEQ ID NO 30
<211> LENGTH: 14
<212> TYPE: PRT
<213> ORGANISM: Artificial Sequence
<220> FEATURE:
<221> NAME/KEY: MOD_RES
<222> LOCATION: (3)
<223> OTHER INFORMATION: Phe or Leu
<220> FEATURE:
<221> NAME/KEY: MOD_RES
<222> LOCATION: (4)
<223> OTHER INFORMATION: Ile or Val
<220> FEATURE:
<221> NAME/KEY: MOD_RES
<222> LOCATION: (7)
<223> OTHER INFORMATION: Leu or Met
<220> FEATURE:
<221> NAME/KEY: MOD_RES
<222> LOCATION: (8)
```

```
-continued

<223> OTHER INFORMATION: Gly, Ser or Thr
<220> FEATURE:
<221> NAME/KEY: MOD_RES
<222> LOCATION: (10)
<223> OTHER INFORMATION: Pro, Ser or Asn
<220> FEATURE:
<221> NAME/KEY: MOD_RES
<222> LOCATION: (13)
<223> OTHER INFORMATION: Lys or Arg
<220> FEATURE:
<221> NAME/KEY: MOD_RES
<222> LOCATION: (14)
<223> OTHER INFORMATION: Gln or Arg
<220> FEATURE:
<223> OTHER INFORMATION: Description of Artificial Sequence: Consensus
      sequence

<400> SEQUENCE: 30

His Ser Xaa Xaa Leu Ile Xaa Xaa Asn Xaa Lys Leu Xaa Xaa
 1               5                  10

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide translocation domain

<400> SEQUENCE: 31

Met Asn Gly Thr Glu Gly Pro Asn Phe Tyr Val Pro Phe Ser Asn Lys
 1               5                   10                  15

Thr Gly Val Val
            20
```

HT2R54 RECEPTOR POLYPEPTIDES AND NUCLEIC ACID SEQUENCES

CROSS REFERENCE TO RELATED APPLICATIONS

This application is a continuation of U.S. application Ser. No. 10/724,209 filed on Dec. 1, 2003, now U.S. Pat. No. 7,393,654, which is a divisional of U.S. application Ser. No. 09/825,882, now U.S. Pat. No. 7,105,650 filed Apr. 5, 2001, which claims priority to U.S. Provisional Application No. 60/195,532, filed Apr. 7, 2000, and U.S. Provisional Application No. 60/247,014, filed Nov. 13, 2000, which are incorporated by reference in their entireties.

FIELD OF THE INVENTION

The invention relates to newly identified mammalian chemosensory G Protein-Coupled Receptors, to a family of such receptors, and to the genes and cDNA encoding said receptors. More particularly, the invention relates to newly identified mammalian chemosensory G Protein-Coupled Receptors active in taste signaling, to a family of such receptors, to the genes and cDNA encoding said receptors, and to methods of using such receptors, genes, and cDNA in the analysis and discovery of taste modulators.

DESCRIPTION OF THE RELATED ART

The taste system provides sensory information about the chemical composition of the external world. Taste transduction is one of the most sophisticated forms of chemical-triggered sensation in animals, and is found throughout the animal kingdom, from simple metazoans to the most complex of vertebrates. Mammals are believed to have five basic taste modalities: sweet, bitter, sour, salty, and umami (the taste of monosodium glutamate).

Each taste modality is believed to be mediated by distinct transduction pathways. These pathways are believed to be mediated by receptors, e.g., metabotropic or ionotropic receptors, expressed in subsets of taste receptor cells. For instance, some tastes are believed to be mediated by G Protein-Coupled Receptors, while other tastes are believed to be mediated by channel proteins (see, e.g. Kawamura et al., *Introduction to Umami: A Basic Taste* (1987); Kinnamon et al., *Ann. Rev. Physiol.,* 54:715-31 (1992); Lindemann, *Physiol. Rev.,* 76:718-66 (1996); Stewart et al., *Am. J. Physiol.,* 272:1-26 (1997)).

In mammals, taste receptor cells are assembled into taste buds that are distributed into different papillae in the tongue epithelium. Circumvallate papillae, found at the very back of the tongue, contain hundreds to thousands of taste buds. By contrast, foliate papillae, localized to the posterior lateral edge of the tongue, contain dozens to hundreds of taste buds. Further, fungiform papillae, located at the front of the tongue, contain only a small number of taste buds.

Each taste bud, depending on the species, contains 50-150 cells, including precursor cells, support cells, and taste receptor cells. See, e.g., Lindemann, *Physiol. Rev.,* 76:718-66 (1996). Receptor cells are innervated at their base by afferent nerve endings that transmit information to the taste centers of the cortex through synapses in the brain stem and thalamus. Elucidating the mechanisms of taste cell signaling and information processing is important to understanding the function, regulation, and perception of the sense of taste.

Numerous physiological studies in animals have shown that taste receptor cells may selectively respond to different chemical stimuli (see, e.g., Akabas et al., *Science,* 242:1047-50 (1988); Gilbertson et al., *J. Gen. Physiol.,* 100:803-24 (1992); Bernhardt et al., *J. Physiol.,* 490:325-36 (1996); Cummings et al, *J. Neurophysiol.,* 75:1256-63 (1996)). More particularly, cells that express taste receptors, when exposed to certain chemical stimuli, elicit taste sensation by depolarizing to generate an action potential. The action potential is believed to trigger the release of neurotransmitters at gustatory afferent neuron synapses, thereby initiating signaling along neuronal pathways that mediate taste perception (see, e.g., Roper, *Ann. Rev. Neurosci.,* 12:329-53 (1989)). Nonetheless, at present, the means by which taste sensations are elicited remains poorly understood (see, e.g., Margolskee, *BioEssays,* 15:645-50 (1993); Avenet et al., *J. Membrane Biol.,* 112:1-8 (1989)).

As described above, taste receptors specifically recognize molecules that elicit specific taste sensation. These molecules are also referred to herein as "tastants." Many taste receptors belong to the 7-transmembrane receptor superfamily (Hoon et al., *Cell* 96:451 (1999); Adler et al., *Cell,* 100:693 (2000)), which are also known as G Protein-Coupled Receptors (GPCRs). G Protein-Coupled Receptors control many physiological functions, such as endocrine function, exocrine function, heart rate, lipolysis, and carbohydrate metabolism. The biochemical analysis and molecular cloning of a number of such receptors has revealed many basic principles regarding the function of these receptors.

For example, U.S. Pat. No. 5,691,188 describes how upon a ligand binding to a GPCR, the receptor presumably undergoes a conformational change leading to activation of the G Protein. G Proteins are comprised of three subunits: a guanyl nucleotide binding α subunit, a β subunit, and a γ subunit. G Proteins cycle between two forms, depending on whether GDP or GTP is bound to the α subunit. When GDP is bound, the G Protein exists as a heterotrimer: the Gαβγ complex. When GTP is bound, the α subunit dissociates from the heterotrimer, leaving a Gβγ complex. When a Gαβγ complex operatively associates with an activated G Protein-Coupled Receptor in a cell membrane, the rate of exchange of GTP for bound GDP is increased and the rate of dissociation of the bound Gα subunit from the Gαβγ complex increases. The free Gα subunit and Gβγ complex are thus capable of transmitting a signal to downstream elements of a variety of signal transduction pathways. These events form the basis for a multiplicity of different cell signaling phenomena, including for example the signaling phenomena that are identified as neurological sensory perceptions such as taste and/or smell.

Complete or partial sequences of numerous human and other eukaryotic chemosensory receptors are currently known (see, e.g., Pilpel, Y. et al, *Protein Science,* 8:969-77 (1999); Mombaerts, P., *Annu. Rev. Neurosci.,* 22:487-50 (1999); EP0867508A2; U.S. Pat. No. 5,874,243; WO 92/17585; WO 95/18140; WO 97/17444; WO 99/67282) Although much is known about the psychophysics and physiology of taste cell function, very little is known about the molecules and pathways that mediate its sensory signaling response. The identification and isolation of novel taste receptors and taste signaling molecules could allow for new methods of chemical and genetic modulation of taste transduction pathways. For example, the availability of receptor and channel molecules could permit screening for high affinity agonists, antagonists, inverse agonists, and modulators of taste activity. Such taste modulating compounds could be useful in the pharmaceutical and food industries to improve the taste of a variety of consumer products, or to block undesirable tastes, e.g. bitter tastes, in certain products.

SUMMARY OF THE INVENTION

In part, the present invention addresses the need for better understanding of the interactions between chemosensory receptors and chemical stimuli. Thus, the present invention provides, among other things, novel taste receptors, and methods for utilizing such receptors, and the genes and cDNAs encoding such receptors, to identify molecules that can be used to modulate taste transduction.

More particularly, the invention relates to a recently discovered family of G Protein-Coupled Receptors, and to the genes and cDNAs encoding said receptors. The receptors are thought to be primarily involved in bitter taste transduction, but can be involved in transducing signals from other taste modalities as well.

The invention provides methods for representing the perception of taste and/or for predicting the perception of taste in a mammal, including in a human. Preferably, such methods may be performed by using the receptors and genes encoding said receptors disclosed herein.

Toward that end, it is an object of the invention to provide a new family of mammalian G Protein-Coupled Receptors, herein referred to as T2Rs, active in taste perception. It is another object of the invention to provide fragments and variants of such T2Rs that retain tastant-binding activity.

It is yet another object of the invention to provide nucleic acid sequences or molecules that encode such T2Rs, fragments, or variants thereof.

It is still another object of the invention to provide expression vectors which include nucleic acid sequences that encode such T2Rs, or fragments or variants thereof, which are operably linked to at least one regulatory sequence such as a promoter, enhancer, or other sequence involved in positive or negative gene transcription and/or translation.

It is still another object of the invention to provide human or non-human cells that functionally express at least one of such T2Rs, or fragments or variants thereof. It is still another object of the invention to provide T2R fusion proteins or polypeptides that include at least a fragment of at least one of such T2Rs.

It is another object of the invention to provide an isolated nucleic acid molecule encoding a T2R polypeptide comprising a nucleic acid sequence that is at least 50%, preferably 75%, 85%, 90%, 95%, 96%, 97%, 98%, or 99% identical to a nucleic acid sequence selected from the group consisting of: SEQ ID NOS: 1, 3, 5, 7, 9, 11, 13, 15, 17, 19, and 23, and conservatively modified variants thereof.

It is a further object of the invention to provide an isolated nucleic acid molecule comprising a nucleic acid sequence that encodes a polypeptide having an amino acid sequence at least 35 to 50%, and preferably 60%, 75%, 85%, 90%, 95%, 96%, 97%, 98%, or 99% identical to an amino acid sequence selected from the group consisting of: SEQ ID NOS: 2, 4, 6, 8, 10, 12, 14, 16, 18, 20, and 24, and conservatively modified variants thereof, wherein the fragment is at least 20, preferably 40, 60, 80, 100, 150, 200, or 250 amino acids in length. Optionally, the fragment can be an antigenic fragment that binds to an anti-T2R antibody.

It is still a further object of the invention to provide an isolated polypeptide comprising a variant of said fragment, wherein there is a variation in at most 10, preferably 5, 4, 3, 2, or 1 amino acid residues.

It is still another object of the invention to provide agonists or antagonists of such T2Rs, or fragments or variants thereof.

It is yet another object of the invention to provide methods for representing the perception of taste and/or for predicting the perception of taste in a mammal, including in a human. Preferably, such methods may be performed by using the T2Rs, or fragments or variants thereof, and genes encoding such T2Rs, or fragments or variants thereof, disclosed herein.

It is yet another object of the invention to provide novel molecules or combinations of molecules that elicit a predetermined taste perception in a mammal.

Such molecules or compositions can be generated by determining a value of taste perception in a mammal for a known molecule or combinations of molecules; determining a value of taste perception in a mammal for one or more unknown molecules or combinations of molecules; comparing the value of taste perception in a mammal for one or more unknown compositions to the value of taste perception in a mammal for one or more known compositions; selecting a molecule or combination of molecules that elicits a predetermined taste perception in a mammal; and combining two or more unknown molecules or combinations of molecules to form a molecule or combination of molecules that elicits a predetermined taste perception in a mammal. The combining step yields a single molecule or a combination of molecules that elicits a predetermined taste perception in a mammal.

It is still a further object of the invention to provide a method of screening one or more compounds for the presence of a taste detectable by a mammal, comprising: a step of contacting said one or more compounds with at least one of the disclosed T2Rs, fragments or variants thereof, preferably wherein the mammal is a human.

It is another object of the invention to provided a method for simulating a taste, comprising the steps of: for each of a plurality of T2Rs, or fragments of variants thereof disclosed herein, preferably human T2Rs, ascertaining the extent to which the T2R interacts with the tastant; and combining a plurality of compounds, each having a previously ascertained interaction with one or more of the T2Rs, in amounts that together provide a receptor-stimulation profile that mimics the profile for the taste. Interaction of a tastant with a T2R can be determined using any of the binding or reporter assays described herein. The plurality of compounds may then be combined to form a mixture. If desired, one or more of the plurality of the compounds can be combined covalently. The combined compounds substantially stimulate at least 50%, 60%, 70%, 75%, 80% or 90% or all of the receptors that are substantially stimulated by the tastant.

In yet another aspect of the invention, a method is provided wherein a plurality of standard compounds are tested against a plurality of T2Rs, or fragments or variants thereof, to ascertain the extent to which the T2Rs each interact with each standard compound, thereby generating a receptor stimulation profile for each standard compound. These receptor stimulation profiles may then be stored in a relational database on a data storage medium. The method may further comprise providing a desired receptor-stimulation profile for a taste; comparing the desired receptor stimulation profile to the relational database; and ascertaining one or more combinations of standard compounds that most closely match the desired receptor-stimulation profile. The method may further comprise combining standard compounds in one or more of the ascertained combinations to simulate the taste.

It is a further object of the invention to provide a method for representing taste perception of a particular substance in a mammal, comprising the steps of: providing values $X_1$ to $X_n$ representative of the quantitative stimulation of each of n T2Rs of said vertebrate, where n is greater than or equal to 4, n is greater than or equal to 12; n is greater than or equal to 24, or n is greater than or equal to 40; and generating from said values a quantitative representation of taste perception. The T2Rs may be a taste receptor disclosed herein, or fragments or variants thereof, the representation may constitute a point or a volume in n-dimensional space, may constitute a graph or a spectrum, or may constitute a matrix of quantitative representations. Also, the providing step may comprise contacting a plurality of recombinantly produced T2Rs, or fragments or variants thereof, with a test composition and quantitatively measuring the interaction of said composition with said receptors.

It is a related object of the invention to provide a method for predicting the taste perception in a mammal generated by one or more molecules or combinations of molecules yielding unknown taste perception in a mammal, comprising the steps of: providing values $X_1$ to $X_n$ representative of the quantitative stimulation of each of n T2Rs of said vertebrate, where n is greater than or equal to 4 n is greater than or equal to 12; n is greater than or equal to 24, or n is greater than or equal to 40; for one or more molecules or combinations of molecules yielding known taste perception in a mammal; and generating from said values a quantitative representation of taste perception in a mammal for the one or more molecules or combinations of molecules yielding known taste perception in a mammal, providing values $X_1$ to $X_n$ representative of the quantitative stimulation of each of n T2Rs of said vertebrate, where n is greater than or equal to 4, n is greater than or equal to 12; n is greater than or equal to 24, or n is greater than or equal to 40; for one or more molecules or combinations of molecules yielding unknown taste perception in a mammal; and generating from said values a quantitative representation of taste perception in a mammal for the one or more molecules or combinations of molecules yielding unknown taste perception in a mammal, and predicting the taste perception in a mammal generated by one or more molecules or combinations of molecules yielding unknown taste perception in a mammal by comparing the quantitative representation of taste perception in a mammal for the one or more molecules or combinations of molecules yielding unknown taste perception in a mammal to the quantitative representation of taste perception in a mammal for the one or more molecules or combinations of molecules yielding known taste perception in a mammal. The T2Rs used in this method may include a taste receptor, or fragment or variant thereof, disclosed herein.

DETAILED DESCRIPTION OF THE INVENTION

The invention thus provides isolated nucleic acid molecules encoding taste-cell-specific G Protein-Coupled Receptors ("GPCRs"), and the polypeptides they encode. These nucleic acid molecules and the polypeptides that they encode are members of the T2R family of taste-cell-specific GPCRs. More particularly, the recent identification of the T2R gene family, which encodes candidate bitter taste receptors, database accession numbers AF227129-AF227149 and AF240765-AF240768, prompted the search for, and identification of related genes in public nucleotide sequence databases. The present invention relates to newly identified members of this family. Further information regarding the T2R family can be found in Adler et al., *Cell*, 100:693-702 (2000) and Chandrashekar et al., *Cell*, 100:703-11 (200), both of which are herein incorporated by reference in their entireties.

Nucleic acids encoding the T2R proteins and polypeptides of the invention can be isolated from a variety of sources, genetically engineered, amplified, synthesized, and/or expressed recombinantly according to the methods disclosed in WO 0035374, which is herein incorporated by reference in its entirety.

More particularly, the invention provides nucleic acids encoding a novel family of taste-cell-specific G Protein-Coupled Receptors. These nucleic acids and the receptors that they encode are referred to as members of the "T2R" family of taste-cell-specific G Protein-Coupled Receptors ("GPCRs"). These taste-cell-specific GPCRs are believed to be components of the taste transduction pathway, specifically, the bitter taste transduction pathway, and are involved in the taste detection of substances such as the bitter substances, 6-n-propylthiouracil (PROP), sucrose octaacetate (soa), raffinose undecaacetate (rua), denatonium, copper glycinate, and quinine. However, the T2Rs may be involved in other taste modalities as well.

Further, it is believed that T2R family members may act in combination with other T2R family members, other taste-cell-specific GPCRs, or a combination thereof, to thereby effect chemosensory taste transduction. For instance, it is believed that T2R family members maybe co-expressed within the same taste receptor cell type, and the co-expressed receptors may physically interact to form a heterodimeric taste receptor. Alternatively, the co-expressed receptors may both independently bind to the same type of ligand, and their combined binding may result in a specific perceived taste sensation.

The invention also provides methods of screening for modulators, e.g., activators, inhibitors, stimulators, enhancers, agonists, and antagonists, of these novel taste-cell-specific GPCRs. Such modulators of taste transduction are useful for pharmacological and genetic modulation of taste signaling pathways. These methods of screening can be used to identify high affinity agonists and antagonists of taste cell activity. These modulatory compounds can then be used in the food and pharmaceutical industries to customize taste, for example, to decrease or mask the bitter taste of foods or drugs.

Thus, the invention provides assays for taste modulation, where members of the T2R family act as direct or indirect reporter molecules of the effect of modulators on taste transduction. GPCRs can be used in assays, e.g., to measure changes in ligand binding, ion concentration, membrane potential, current flow, ion flux, transcription, signal transduction, receptor-ligand interactions, second messenger concentrations, in vitro, in vivo, and ex vivo. In one embodiment, members of the T2R family can be used as indirect reporters via attachment to a second reporter molecule such as green fluorescent protein (see, e.g., Mistili & Spector, *Nature Biotechnology*, 15:961-64 (1997)). In another embodiment, T2R family members are recombinantly expressed in cells, and modulation of taste transduction via GPCR activity can be assayed by measuring changes in $Ca^{2+}$ levels and other intracellular messengers such as cAMP, cGMP, or IP3.

In a preferred embodiment, a T2R polypeptide is expressed in an eukaryotic cell as a chimeric receptor with a heterologous sequence that facilitates plasma membrane trafficking or maturation and targeting through the secretory pathway. In a preferred embodiment, the heterologous sequence is a rhodopsin sequence, such as an N-terminal fragment of a rhodopsin. Such chimeric T2R receptors can be expressed in any eukaryotic cell, such as HEK-293 cells. Preferably, the cells comprise a functional G Protein, e.g., Gα15, that is capable of coupling the chimeric receptor to an intracellular signaling pathway or to a signaling protein such as phospholipase C. Activation of such chimeric receptors in such cells can be detected using any-standard method, such as by detecting changes in intracellular calcium by detecting FURA-2- dependent fluorescence in the cell. If host cells do not express an appropriate G Protein, they may be transfected with a gene encoding a promiscuous G Protein such as those described in U.S. Ser. No. 60/243,770, which is herein incorporated by reference in its entirety.

Methods of assaying for modulators of taste transduction can include in vitro ligand binding assays using T2R polypeptides, portions thereof, such as the extracellular domain, transmembrane region, or combinations thereof, or chimeric proteins comprising one or more domains of a T2R family member; oocyte, primary cell or tissue culture cell T2R gene expression, or expression of T2R fragments or fusion proteins, such as rhodopsin fusion proteins; phosphorylation and dephosphorylation of T2R family members; G Protein binding to GPCRs; arrestin binding; internalization; ligand binding assays; voltage, membrane potential and conductance changes; ion flux assays; changes in intracellular second messengers such as cGMP, cAMP and IP3; changes in intracellular $Ca^{2+}$ levels; and neurotransmitter release.

Further, the invention provides methods of detecting T2R nucleic acid and protein expression, allowing investigation of taste transduction regulation and specific identification of taste receptor cells. T2R family members also provide useful nucleic acid probes for paternity and forensic investigations. T2R genes are also useful as a nucleic acid probes for identifying taste receptor cells, such as foliate, fungiform, circumvallate, geschmackstreifen, and epiglottis taste receptor cells, in particular bitter-taste receptive, gustducin expressing cells. Furthermore, the nucleic acids and the polypeptides they encode can be used as probes to dissect taste-induced behaviors.

T2R polypeptides can also be used to generate monoclonal and polyclonal antibodies useful for identifying taste receptor cells. Taste receptor cells can be identified using techniques such as reverse transcription and amplification of mRNA, isolation of total RNA or poly A+ RNA, northern blotting, dot blotting, in situ hybridization, RNase protection, S1 digestion, probing DNA microchip arrays, western blots, and the like.

The T2R genes and the polypeptides they encode comprise a family of related taste-cell-specific G Protein-Coupled Receptors. Within the genome, these genes are present either alone or within one of several gene clusters. One gene cluster, located at human genomic region 12p13, comprises at least 24 genes, and a second cluster, located at 7q33, comprises at least 7 genes. In total, more than 60 distinct T2R family members have been identified from difference organisms, including several putative pseudogenes. It is estimated that the human genome may include approximately 40 distinct T2R genes, encoding about 30 functional human receptors.

Some of the T2R genes have been associated with previously mapped loci implicated in the control of bitter taste. For example, the human T2R1 is located at human interval 5p15, precisely where a locus that influences the ability to taste the substance PROP has previously been mapped (see Reed et al., Am. J. Hum. Genet., 64:1478-80 (1999)). In addition, the human gene cluster found at genomic region 12p13 corresponds to a region of mouse chromosome 6 that has been shown to contain numerous bitter-tasting genes, that are believed to influence taste perception or sensation including e.g., sucrose octaacetate, raffinose, undecaacetate cycloheximide, and quinine (see, e.g., Lush et al., Genet. Res., 6:167-74 (1995)). These associations suggest that the T2R genes are involved in the taste detection of various substances, in particular bitter substances. In addition, mouse T2R5 is specifically receptive to cycloheximide, and mutations in the mT2R5 gene have been hypothesized to produce a cycloheximide-non-tasting phenotype. Similarly, human T2R4 and mouse T2R8 are specifically responsive to both denatonium and PROP.

Functionally, the T2R genes comprise a family of related seven transmembrane G Protein-Coupled Receptors which are believed to be involved in taste transduction and which may interact with a G Protein to mediate taste signal transduction (see, e.g., Fong, *Cell Signal*, 8:217 (1996); Baldwin, *Curr Opin. Cell Biol.*, 6:180 (1994)). In particular, T2Rs are believed to interact in a ligand-specific manner with the G Protein gustducin.

Structurally, the nucleotide sequences of T2R family members encode a family of related polypeptides comprising an extracellular domain, seven transmembrane domains, and a cytoplasmic domain. Related T2R family genes from other species typically will share about 20-30% nucleotide sequence identity over a region of at least about 50 nucleotides in length, optionally 100, 200, 500, or more nucleotides in length to SEQ ID NOS: 1, 3, 5, 7, 9, 11, 13, 15, 17, 19, and 23, or conservatively modified variants thereof; or encode polypeptides sharing at least about 30-40% amino acid sequence identity over an amino acid region at least about 25 amino acids in length, optionally 50 to 100 amino acids in length to SEQ ID NOS: 2, 4, 6, 8, 10, 12, 14, 16, 18, 20, and 24, or conservatively modified variants thereof. It has been shown that T2R genes are selectively expressed in subsets of taste receptor cells of the tongue, palate epithelium, foliate, geschmackstreifen, and epiglottis. In contrast, studies have shown that T2Rs are less often expressed in fungiform papillae. Further, it has been shown that T2Rs are selectively expressed in gustducin-positive cells.

Several consensus amino acid sequences or domains have also been identified that are characteristic of T2R family members. Particularly, it has been found that T2R family members typically comprise a sequence having at least about 50%, optionally 55%, 60%, 65%, 70%, 75%, 80%, 85%, 90%, 95%, or higher, identity to T2R Transmembrane Region I, T2R Transmembrane Region II, T2R Transmembrane Region III, T2R Transmembrane Region IV, T2R Transmembrane Region V, and T2R Transmembrane Region VII. These conserved domains thus can be used to identify members of the T2R family, by identity, specific hybridization or amplification, or specific binding by antibodies raised against a domain. Such T2R transmembrane regions have the following amino acid sequences:

```
T2R Family Consensus Sequence 1:
                                          (SEQ ID NO: 25)
E(F/A)(I/V/L)(V/L)G(I/V)(L/V)GN(G/T)FI(V/A)LVNC (I/M)DW T2R Family Consensus Sequence 2:
                                          (SEQ ID NO: 26)
(D/G)(F/L)(I/L)L(T/I)(G/A/S)LAISRI(C/G/F)L T2R Family Consensus Sequence 3:
                                          (SEQ ID NO: 27)
NH(L/F)(S/T/N)(L/I/V)W(F/L)(A/T)T(C/S/N)L(S/N/G)

(I/V)

T2R Family Consensus Sequence 4:
                                          (SEQ ID NO: 28)
FY(F/C)LKIA(N/S)FS(H/N)(P/S)(L/I/V)FL(W/Y)LK T2R Family Consensus Sequence 5:
                                          (SEQ ID NO: 29)
LLI(I/F/V)SLW(K/R)H(S/T)(K/R)(Q/K)(M/I)(Q/K)
```

-continued

T2R Family Consensus Sequence 6:
(SEQ ID NO: 30)
HS(F/L)(I/V)LI(L/M)(G/S/T)N(P/S/N)KL(K/R)(Q/R)

Specific regions of human T2R nucleotide and amino acid sequences may be used to identify polymorphic variants or alleles or homologs comprised in humans or other species. This identification can be effected in vitro, e.g., under stringent hybridization conditions or PCR (e.g., using primers encoding the T2R consensus sequences identified above) and sequencing, or by using the sequence information in a computer system for comparison with other nucleotide sequences. Typically, identification of polymorphic variants or alleles of T2R family members can be made by comparing an amino acid sequence of about 25 amino acids or more, e.g., 50-100 amino acids. Amino acid identity of approximately 30-40%, optionally 50-60%, 65%, 70%, 75%, 80%, 85%, 90%, or 95-99% or above suggests that a protein is a polymorphic variant, or allele, or a homolog or ortholog of a T2R family member. Sequence identity can be calculated by the methods disclosed infra. It can be determined almost definitely that a positive T2R gene falls within the T2R family based on the additional presence of at least one conserved sequence that is identical or at least 75% identical to the previously identified T2R family consensus sequences. Sequence comparison can be performed using any of the sequence comparison algorithms discussed below. Antibodies that bind specifically to T2R polypeptides or a conserved region thereof can also be used to identify alleles, interspecies homologs, and polymorphic variants of T2R proteins.

Polymorphic variants, or alleles, and related T2R homologs or orthologs can be confirmed by examining taste-cell-specific expression of the putative T2R polypeptide. Typically, T2R polypeptides having an amino acid sequence disclosed herein can be used as a positive control in comparison to the putative T2R protein to demonstrate the identification of an allele or homolog of the T2R family member. Such homologs or alleles will similarly posses the seven transmembrane structure of a G Protein-Coupled Receptor.

Nucleotide and amino acid sequence information for T2R family members may also be used to construct models of taste-cell-specific polypeptides in a computer system. These models are subsequently used to identify compounds that can activate or inhibit T2R receptor proteins. Such compounds that modulate the activity of T2R family members can be used to investigate the role of T2R genes and polypeptides in taste transduction.

The isolation of T2R family members provides a means for assaying for inhibitors and activators of taste transduction. Biologically active T2R proteins are useful for testing inhibitors and activators of T2R as taste transducers, especially bitter taste transducers, using in vivo (animal based assays) and in vitro assays that measure, e.g., ligand binding; phosphorylation and dephosphorylation; binding to G Proteins; G Protein activation; regulatory molecule binding; voltage, membrane potential and conductance changes; ion flux; intracellular second messengers such as cGMP, cAMP, IP3; and intracellular calcium levels. Such activators and inhibitors identified using T2R family members can be used to further study taste transduction and to identify specific taste agonists and antagonists. Such activators and inhibitors are useful as pharmaceutical and food agents for customizing taste, for example to decrease the bitter taste of foods or pharmaceuticals.

The present invention also provides assays, preferably high throughput assays, to identify molecules that interact with and/or modulate a T2R polypeptide. In numerous assays, a particular portion of a T2R family member will be used, e.g. an extracellular, transmembrane, or intracellular or region. In numerous embodiments, an extracellular domain, transmembrane region, or combination thereof is bound to a solid substrate, and used, e.g., to isolate ligands, agonists, inverse agonists, antagonists, or any other molecules that can bind to and/or modulate the activity of an extracellular or transmembrane region of a T2R polypeptide.

In certain embodiments, a region of a T2R polypeptide, e.g., an extracellular, transmembrane, or intracellular region, is fused to a heterologous polypeptide, thereby forming a chimeric polypeptide, e.g., a chimeric polypeptide with GPCR activity. Such chimeric polypeptides are useful, e.g., in assays to identify ligands, agonists, inverse agonists, antagonists, or other modulators of a T2R polypeptide. In addition, such chimeric polypeptides are useful to create novel taste receptors with novel ligand binding specificity, modes of regulation, signal transduction pathways, or other such properties, or to create novel taste receptors with novel combinations of ligand binding specificity, modes of regulation, signal transduction pathways, etc. Also T2R nucleic acids and expression of T2R polypeptides can be used to create topological maps of the tongue that potentially can be used to study the relation of tongue taste receptor cells to taste sensory neurons in the brain. In particular, methods of detecting T2Rs can potentially be used to identify taste cells that are sensitive to bitter tasting substances. Chromosome localization of the genes encoding human T2R genes can also potentially be used to identify diseases, mutations, and traits caused by, or associated with T2R family members.

Generally, the invention provides isolated nucleic acid molecules of the T2R gene family and the taste receptors they encode. The present invention also includes not only nucleic acid and polypeptide sequences having the specified amino acid sequences, but also fragments, particularly fragments of, for example, 40, 60, 80, 100, 150, 200, or 250 nucleotides, or more, as well as protein fragments of, for example, 10, 20, 30, 50, 70, 100, or 150 amino acids, or more.

Various conservative mutations and substitutions are envisioned to be within the scope of the invention. For instance, it would be within the level of skill in the art to perform amino acid substitutions using known protocols of recombinant gene technology including PCR, gene cloning, site-directed mutagenesis of cDNA, transfection of host cells, and in-vitro transcription. The variants can then be screened for functional activity.

More particularly, specific regions of the nucleic acid sequences disclosed herein, and the polypeptides they encode, may be used to identify polymorphic variants, interspecies homologs, and alleles of the sequences. This identification can be made in vitro, e.g., under stringent hybridization conditions, PCR, and sequencing, or by using the sequence information in a computer system for comparison with other nucleic acid sequences. Different alleles of T2R genes within a single species population will also be useful in determining whether differences in allelic sequences correlate to differences in taste perception between members of the population.

The nucleic acid molecules of the present invention are generally intronless and encode putative T2R proteins generally having lengths of approximately 300 residues and are comprised of seven transmembrane regions, as predicted by hydrophobicity plotting analysis, suggesting that they belong to the G Protein-Coupled Receptor (7TM) superfamily. In addition to the overall structural similarity, each of the T2Rs identified herein has a characteristic sequence signature of a T2R family member. In particular, all sequences contain very close matches to the T2R family consensus sequences identified above. Combination of all the above mentioned structural features of the identified genes and encoded proteins strongly suggests that they represent novel members of the T2R receptor family.

It is also hypothesized that that T2R receptors and their genes can be used, alone or in combination with other types of taste receptors, in developing detection systems and assays for chemically identifying distinct types of molecules specifically recognized by these receptors, as well as for diagnostic and research purposes.

The nucleic acid sequences of the invention and other nucleic acids used to practice this invention, whether RNA, cDNA, genomic DNA, vectors, viruses or hybrids thereof, may be isolated from a variety of sources, genetically engineered, amplified, and/or expressed recombinantly. Any recombinant expression system can be used, including, in addition to mammalian cells, e.g., bacterial, yeast, insect, or plant systems.

A. Identification of T2Rs

The amino acid sequences of the T2R proteins and polypeptides of the invention can be identified by putative translation of the coding nucleic acid sequences. These various amino acid sequences and the coding nucleic acid sequences may be compared to one another or to other sequences according to a number of methods. In a particular embodiment, the pseudogenes disclosed herein can be used to identify functional alleles or related genes in genomic databases known in the art.

For example, in sequence comparison, typically one sequence acts as a reference sequence, to which test sequences are compared. When using a sequence comparison algorithm, test and reference sequences are entered into a computer, subsequence coordinates are designated, if necessary, and sequence algorithm, program parameters are designated. Default program parameters can be used, as described below for the BLASTN and BLASTP programs, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith & Waterman, *Adv. Appl. Math.,* 2:482 (1981), by the homology alignment algorithm of Needleman & Wunsch, *J. Mol. Biol.* 48:443 (1970), by the search for similarity method of Pearson & Lipman, *PNAS,* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g. *Current Protocols in Molecular Biology* (Ausubel et al., eds. 1995 supplement)).

A preferred example of an algorithm that is suitable for determining percent sequence identity and sequence similarity are the BLAST and BLAST 2.0 algorithms, which are described in Altschul et al., *Nuc. Acids Res.,* 25:3389-402 (1977) and Altschul et al., *J. Mol. Biol.,* 215:403-10 (1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive valued threshold score T when aligned with a word of the same length in a database sequence. T is referred to as the neighborhood word score threshold (Altschul et al., Altschul et al., Nuc. Acids Res., 25:3389-402 (1977) and Altschul et al., *J. Mol. Biol.,* 215: 403-10 (1990)). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUTM62 scoring matrix (see Henikoff & Henikoff, *PNAS,* 89:10915 (1989)) alignments (B) of 50, expectation (E) of 10, M=5, N=−4, and a comparison of both strands.

Another example of a useful algorithm is PILEUP. PILEUP creates a multiple sequence alignment from a group of related sequences using progressive, pairwise alignments to show relationship and percent sequence identity. It also plots a so-called "tree" or "dendogram" showing the clustering relationships used to create the alignment (see, e.g., FIG. 2). PILEUP uses a simplification of the progressive alignment method of Feng & Doolittle, *J Mol. Evol.,* 35:351-60 (1987). The method used is similar to the method described by Higgins & Sharp, *CABIOS* 5:151-53 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 Devereaux et al., *Nuc. Acids Res.,* 12:387-95 (1984). Comparison of these protein sequences to all known proteins in the public sequence databases using BLASTP algorithm revealed their strong homology to the members of the T2R family, each of the T2R family sequences having at least 50%, and preferably at least 55%, at least 60%, at least 65%, and most preferably at least 70%, amino acid identity to at least one known member of the family.

B. Definitions

As used herein, the following terms have the meanings ascribed to them unless specified otherwise.

"Taste cells" include neuroepithelial cells that are organized into groups to form taste buds of the tongue, e.g., foliate, fungiform, and circumvallate cells (see, e.g., Roper et al., Ann. Rev. Neurosci. 12:329-353 (1989)). Taste cells are also found in the palate, and other tissues such as the esophagus and the stomach.

"T2R" refers to one or more members of a family of G Protein-Coupled Receptors that are selectively expressed in taste cells of the tongue and palate epithelium, such as foliate, geschmackstreifen, epiglottis, fungiform, and circumvallate cells, as well as cells of the esophagus, and stomach (see, e.g., Adler et al., Cell, 100:693-702 (2000)). This family is also referred to as the "SF family" (see, e.g., PCT/US00/24821, which is herein incorporated by reference in its entirety). Such taste cells can be identified because they express specific molecules such as gustducin, a taste-cell-specific G Protein, or other taste specific molecules. (McLaughlin et al., Nature, 357:563-69 (1992)). Taste receptor cells can also be identified on the basis of morphology (see, e.g., Roper, supra). T2R family members have the ability to act as receptors for taste transduction. T2R family members are also referred to as the "GR" family, for gustatory receptor, or "SF" family.

"T2R" nucleic acids encode a family of GPCRs with seven transmembrane regions that have "G Protein-Coupled Receptor activity," e.g., they may bind to G Proteins in response to extracellular stimuli and promote production of second messengers such as IP3, cAMP, cGMP, and $Ca^{2+}$ via stimulation of enzymes such as phospholipase C and adenylate cyclase (for a description of the structure and function of GPCRs, see, e.g., Fong, supra, and Baldwin, supra). These nucleic acids encode proteins that are expressed in taste cells, in particular gustducin-expressing taste cells that are responsive to bitter tastants. A single taste cell may contain many distinct T2R polypeptides.

The term "T2R" family therefore includes polymorphic variants, alleles, mutants, and homologs that: (1) have about 30-40% amino acid sequence identity, more specifically about 40, 50, 60, 70, 75, 80, 85, 90, 95, 96, 97, 98, or 99% amino acid sequence identity to SEQ ID NOS: 2, 4, 6, 8, 10, 12, 14, 16, 18, 20, and 24, over a window of about 25 amino acids, optionally 50-100 amino acids; (2) specifically bind to antibodies raised against an immunogen comprising an amino acid sequence selected from the group consisting of SEQ ID NOS: 2, 4, 6, 8, 10, 12, 14, 16, 18, 20, and 24, and conservatively modified variants thereof; (3) specifically hybridize (with a size of at least about 100, optionally at least about 500-1000 nucleotides) under stringent hybridization conditions to a sequence selected from the group consisting of SEQ ID NOS: 1, 3, 5, 7, 9, 11, 13, 15, 17, 19, and 23, and conservatively modified variants thereof; (4) comprise a sequence at least about 40% identical to an amino acid sequence selected from the group consisting of SEQ ED NOS: 2, 4, 6, 8, 10, 12, 14, 16, 18, 20, and 24; or (5) are amplified by primers that specifically hybridize under stringent hybridization conditions to the same sequence as a degenerate primer sets encoding SEQ ID NOS: 25-30.

As previously discussed, while T2R genes exhibit substantial sequence divergence at both the protein and DNA level, all isolated to date have been found to contain comprise certain consensus sequences, in particular regions that are identical or which possess or at least 70-75% sequence identity to the T2R consensus sequence identified previously (SEQ ID NOS: 25-30).

Topologically, certain chemosensory GPCRs have an "N-terminal domain;" "extracellular domains," a "transmembrane domain" comprising seven transmembrane regions, and corresponding cytoplasmic and extracellular loops, "cytoplasmic regions," and a "C-terminal region" (see, e.g., Hoon et al., Cell, 96:541-51 (1999); Buck & Axel, Cell, 65:175-87 (1991)). These regions can be structurally identified using methods known to those of skill in the art, such as sequence analysis programs that identify hydrophobic and hydrophilic domains (see, e.g. Stryer, Biochemistry, (3rd ed. 1988); see also any of a number of Internet based sequence analysis programs, such as those found at dot.imgen.bcm.t-mc.edu). These regions are useful for making chimeric proteins and for in vitro assays of the invention, e.g., ligand binding assays.

"Extracellular domains" therefore refers to the domains of T2R polypeptides that protrude from the cellular membrane and are exposed to the extracellular face of the cell. Such regions would include the "N-terminal domain" that is exposed to the extracellular face of the cell, as well as the extracellular loops of the transmembrane domain that are exposed to the extracellular face of the cell, i.e., the extracellular loops between transmembrane regions 2 and 3, transmembrane regions 4 and 5, and transmembrane regions 6 and 7. The "N-terminal domain" starts at the N-terminus and extends to a region close to the start of the transmembrane region. These extracellular regions are useful for in vitro ligand binding assays, both soluble and solid phase. In addition, transmembrane regions, described below, can also be involved in ligand binding, either in combination with the extracellular region or alone, and are therefore also useful for in vitro ligand binding assays.

"Transmembrane domain," which comprises the seven transmembrane "regions," refers to the domain of T2R polypeptides that lies within the plasma membrane, and may also include the corresponding cytoplasmic (intracellular) and extracellular loops, also referred to as transmembrane "regions." The seven transmembrane regions and extracellular and cytoplasmic loops can be identified using standard methods, as described in Kyte & Doolittle, J. Mol. Biol., 157:105-32 (1982)), or in Stryer, supra.

"Cytoplasmic domains" refers to the domains of T2R proteins that face the inside of the cell, e.g., the "C-terminal domain" and the intracellular loops of the transmembrane domain, e.g., the intracellular loops between transmembrane regions 1 and 2, transmembrane regions 3 and 4, and transmembrane regions 5 and 6. "C-terminal domain" refers to the region that spans from the end of the last transmembrane region to the C-terminus of the protein, and which is normally located within the cytoplasm.

The term "7-transmembrane receptor" means a polypeptide belonging to a superfamily of transmembrane proteins that have seven regions that span the plasma membrane seven times (thus, the seven regions are called "transmembrane" or "TM" domains TM I to TM VII). The families of olfactory and certain taste receptors each belong to this super-family. 7-transmembrane receptor polypeptides have similar and characteristic primary, secondary and tertiary structures, as discussed in further detail below.

The term "ligand-binding region" refers to sequences derived from a chemosensory or taste receptor that substantially incorporates transmembrane domains II to VII (TM II to VI). The region may be capable of binding a ligand, and more particularly, a tastant.

The term "plasma membrane translocation domain" or simply "translocation domain" means a polypeptide domain that is functionally equivalent to an exemplary translocation domain (5'-MNGTEGPNFYVPFSNKTGVV; SEQ ID NO: 31). These peptide domains, when incorporated into the amino terminus of a polypeptide coding sequence, can with great efficiency "chaperone" or "translocate" the hybrid ("fusion") protein to the cell plasma membrane. This particular "translocation domain" was initially derived from the amino terminus of the human rhodopsin receptor polypeptide, a 7-transmembrane receptor. Another translocation domain has been derived from the bovine rhodopsin sequence and is also useful for facilitating translocation. Rhodopsin derived sequences are particularly efficient in translocating 7-transmembrane fusion proteins to the plasma membrane.

"Functional equivalency" means the domain's ability and efficiency in translocating newly translated proteins to the plasma membrane as efficiently as exemplary SEQ ID NO: 31 under similar conditions; relatively efficiencies an be measured (in quantitative terms) and compared, as described herein. Domains falling within the scope of the invention can be determined by routine screening for their efficiency in translocating newly synthesized polypeptides to the plasma membrane in a cell (mammalian, Xenopus, and the like) with the same efficiency as the twenty amino acid long translocation domain SEQ ID NO: 31.

The phrase "functional effects" in the context of assays for testing compounds that modulate T2R family member mediated taste transduction includes the determination of any parameter that is indirectly or directly under the influence of the receptor, e.g., functional, physical and chemical effects. It includes ligand binding, changes in ion flux, membrane potential, current flow, transcription, G Protein binding, GPCR phosphorylation or dephosphorylation, signal transduction, receptor-ligand interactions, second messenger concentrations (e.g., cAMP, cGMP, IP3, or intracellular $Ca^{2+}$), in vitro, in vivo, and ex vivo and also includes other physiologic effects such increases or decreases of neurotransmitter or hormone release.

By "determining the functional effect" is meant assays for a compound that increases or decreases a parameter that is indirectly or directly under the influence of a T2R family member, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, oocyte T2R gene expression; tissue culture cell T2R expression; transcriptional activation of T2R genes; ligand binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like.

"Inhibitors," "activators," and "modulators" of T2R genes or proteins are used interchangeably to refer to inhibitory, activating, or modulating molecules identified using in vitro and in vivo assays for taste transduction, e.g., ligands, agonists, antagonists, and their homologs and mimetics. Inhibitors are compounds that, e.g., bind to, partially or totally block stimulation, decrease, prevent, delay activation, inactivate, desensitize, or down regulate taste transduction, e.g., antagonists. Activators are compounds that, e.g., bind to, stimulate, increase, open, activate, facilitate, enhance activation, sensitize, or up regulate taste transduction, e.g., agonists. Modulators include compounds that, e.g., alter the interaction of a receptor with: extracellular proteins that bind activators or inhibitor (e.g., ebnerin and other members of the hydrophobic carrier family); G Proteins; kinases (e.g., homologs of rhodopsin kinase and beta adrenergic receptor kinases that are involved in deactivation and desensitization of a receptor); and arresting, which also deactivate and desensitize receptors. Modulators include genetically modified versions of T2R family members, e.g., with altered activity, as well as naturally occurring and synthetic ligands, antagonists, agonists, small chemical molecules and the like.

Such assays for inhibitors and activators include, e.g., expressing T2R family members in cells or cell membranes, applying putative modulator compounds in the presence or absence of tastants, e.g., bitter tastants, and then determining the functional effects on taste transduction, as described above. Samples or assays comprising T2R family members that are treated with a potential activator, inhibitor, or modulator are compared to control samples without the inhibitor, activator, or modulator to examine the extent of modulation. Control samples (untreated with modulators) are assigned a relative T2% activity value of 100%. Inhibition of a T2R is achieved when the T2R activity value relative to the control is about 80%, optionally 50% or 25-0%. Activation of a T2R is achieved when the T2R activity value relative to the control is 110%, optionally 150%, optionally 200-500%, or 1000-3000% higher.

The terms "purified," "substantially purified," and "isolated" as used herein refer to the state of being free of other, dissimilar compounds with which the compound of the invention is normally associated in its natural state. Preferably, "purified," "substantially purified," and "isolated" means that the composition comprises at least 0.5%, 1%, 5%, 10%, or 20%, and most preferably at least 50% or 75% of the mass, by weight, of a given sample. In one preferred embodiment, these terms refer to the compound of the invention comprising at least 95% of the mass, by weight, of a given sample. As used herein, the terms "purified," "substantially purified," and "isolated" "isolated," when referring to a nucleic acid or protein, of nucleic acids or proteins, also refers to a state of purification or concentration different than that which occurs naturally in the mammalian, especially human, body. Any degree of purification or concentration greater than that which occurs naturally in the mammalian, especially human, body, including (1) the purification from other associated structures or compounds or (2) the association with structures or compounds to which it is not normally associated in the mammalian, especially human, body, are within the meaning of "isolated." The nucleic acid or protein or classes of nucleic acids or proteins, described herein, may be isolated, or otherwise associated with structures or compounds to which they are not normally associated in nature, according to a variety of methods and processes known to those of skill in the art.

As used herein, the term "isolated," when referring to a nucleic acid or polypeptide refers to a state of purification or concentration different than that which occurs naturally in the mammalian, especially human, body. Any degree of purification or concentration greater than that which occurs naturally in the body, including (1) the purification from other naturally-occurring associated structures or compounds, or (2) the association with structures or compounds to which it is not normally associated in the body are within the meaning of "isolated" as used herein. The nucleic acids or polypeptides described herein may be isolated or otherwise associated with structures or compounds to which they are not normally associated in nature, according to a variety of methods and processed known to those of skill in the art.

As used herein, the terms "amplifying" and "amplification" refer to the use of any suitable amplification methodology for generating or detecting recombinant or naturally expressed nucleic acid, as described in detail, below. For example, the invention provides methods and reagents (e.g., specific oligonucleotide primer pairs) for amplifying (e.g., by polymerase chain reaction, PCR) naturally expressed (e.g., genomic or mRNA) or recombinant (e.g., cDNA) nucleic acids of the invention (e.g., tastant-binding sequences of the invention) in vivo or in vitro.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression cassettes which contain only the minimum elements needed for transcription of the recombinant nucleic acid.

The term "library" means a preparation that is a mixture of different nucleic acid or poly-peptide molecules, such as the library of recombinantly generated sensory, particularly taste receptor ligand-binding regions generated by amplification of nucleic acid with degenerate primer pairs, or an isolated collection of vectors that incorporate the amplified ligand-binding regions, or a mixture of cells each randomly transfected with at least one vector encoding an taste receptor.

The term "nucleic acid" or "nucleic acid sequence" refers to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating, e.g., sequences in which the third position of one or more selected codons is substituted with mixed-base and/or deoxyinosine residues (Batzer et al., *Nucleic Acid Res.*, 19:5081 (1991); Ohtsuka et al., *J. Biol. Chem.*, 260:2605-08 (1985); Rossolini et al., *Mol. Cell. Probes*, 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The "translocation domain," "ligand-binding region", and chimeric receptors compositions described herein also include "analogs," or "conservative variants" and "mimetics" ("peptidomimetics") with structures and activity that substantially correspond to the exemplary sequences. Thus, the terms "conservative variant" or "analog" or "mimetic" refer to a polypeptide which has a modified amino acid sequence, such that the change(s) do not substantially alter the polypeptide's (the conservative variant's) structure and/or activity, as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity.

More particularly, "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein.

For instance, the codons GCA, GCC, GCG and GCU all encode the amino acid alanine. Thus, at every position where an alanine is specified by a codon, the codon can be altered to any of the corresponding codons described without altering the encoded polypeptide.

Such nucleic acid variations are "silent variations," which are one species of conservatively modified variations. Every nucleic acid sequence herein which encodes a polypeptide also describes every possible silent variation of the nucleic-acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence-Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (I); 5) Isoleucine (I), Leucine (L), Methionine (M), Valine (V); and 6) Phenylalanine (F), Tyrosine (Y), Tryptophan (W); (see also, e.g., Creighton, Proteins, W.H. Freeman and Company (1984), Schultz and Schimer, *Principles of Protein Structure*, Springer-Verlag (1979)). One of skill in the art will appreciate that the above-identified substitutions are not the only possible conservative substitutions. For example, for some purposes, one may regard all-charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The terms "mimetic" and "peptidomimetic" refer to a synthetic chemical compound that has substantially the same structural and/or functional characteristics of the polypeptides, e.g., translocation domains, ligand-binding regions, or chimeric receptors of the invention. The mimetic can be either entirely composed of synthetic, non-natural analogs of amino acids, or may be a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N-diisopropylcarbodiimide (DIC). Linking groups that can be an alternative to the traditional amide bond ("peptide bond") linkages include, e.g., ketomethylene e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$), thiazole, retroamide, thioamide, or ester (see, e.g., Spatola, *Chemistry and Biochemistry of Amino Acids, Peptides and Proteins*, Vol. 7, 267-357, Marcell Dekker, *Peptide Backbone Modifications*, NY (1983)). A polypeptide can also be characterized as a mimetic by containing all or some non-natural residues in place of naturally occurring amino acid residues; non-natural residues are well described in the scientific and patent literature.

A "label" or a "detectable moiety" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic; van der Waals, electrostatic, or hydrogen bonds to a label such that the presence of the probe may be detected by detecting the presence of the label bound to the probe.

As used herein a "nucleic acid probe or oligonucieotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" also encompass the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention.

The phrase "selectively (or specifically) hybridizes to" refers to the binding, duplexing, or hybridizing of a molecule only to a particular nucleotide sequence under stringent hybridization conditions when that sequence is present in a complex mixture (e.g. total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence dependent and will be different in different circumstances. Longer sequences hybridize specifically at higher temperatures. An extensive guide to the hybridization of nucleic acids is found in Tijssen, *Techniques in Biochemistry and Molecular Biology—Hybridisation with Nucleic Probes*, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such hybridizations and wash steps can be carried out for, e.g., 1, 2, 5, 10, 15, 30, 60; or more minutes.

Nucleic acids that do not hybridize to each other under stringent conditions are still substantially related if the polypeptides which they encode are substantially related. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such hybridizations and wash steps can be carried out for, e.g., 1, 2, 5, 10, 15, 30, 60, or more minutes. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain (VL) and variable heavy chain (VH) refer to these light and heavy chains respectively.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof is altered, replaced or exchanged with a variable region having a different or altered antigen specificity.

An "anti-T2R" antibody is an antibody or antibody fragment that specifically binds a polypeptide encoded by a T2R gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or, "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein.

For example, polyclonal antibodies raised to a T2R family member from specific species such as rat, mouse, or human can be selected to obtain only those polyclonal antibodies that are specifically immunoreactive with the T2R polypeptide or an immunogenic portion thereof and not with other proteins, except for orthologs or polymorphic variants and alleles of the T2R polypeptide. This selection may be achieved by subtracting out antibodies that cross-react with T2R molecules from other species or other T2R molecules. Antibodies can also be selected that recognize only T2R GPCR family members but not GPCRs from other families. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual*, (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes which contain only the minimum elements needed for transcription of the recombinant nucleic acid.

By "host cell" is meant a cell that contains an expression vector and supports the replication or expression of the expression vector. Host cells may be prokaryotic cells such as E. toll, or eukaryotic cells such as yeast, insect, amphibian, or mammalian cells such as CHO, HeLa, HEK-293, and the like, e.g. cultured cells, explants, and cells in vivo.

C. Isolation and Expression of T2Rs

Isolation and expression of the T2Rs, or fragments or variants thereof, of the invention can be effected by well established cloning procedures using probes or primers constructed based on the T2R nucleic acids sequences disclosed in the application. Related T2R sequences may also be identified from human or other species genomic databases using the sequences disclosed herein and known computer-based search technologies, e.g., BLAST sequence searching. In a particular embodiment, the pseudogenes disclosed herein can be used to identity functional alleles or related genes.

Expression vectors can then be used to infect or transfect host cells for the functional expression of these sequences. These genes and vectors can be made and expressed in vitro or in vivo. One of skill will recognize that desired phenotypes for altering and controlling nucleic acid expression can be obtained by modulating the expression or activity of the genes and nucleic acids (e.g., promoters, enhancers and the like) within the vectors of the invention. Any of the known methods described for increasing or decreasing expression or activity can be used. The invention can be practiced in conjunction with any method or protocol known in the art, which are well described in the scientific and patent literature.

Alternatively, these nucleic acids can be synthesized in vitro by well-known chemical synthesis techniques, as described in, e.g., Carruthers, Cold Spring Harbor *Symp. Quant. Biol.* 47:411-18 (1982); Adams, *Am. Chem. Soc.*, 105:661 (1983); Belousov, *Nucleic Acids Res.* 25:3440-3444 (1997); Frenkel, *Free Radic. Biol. Med.* 19:373-380 (1995); Blommers, *Biochemistry* 33:7886-7896 (1994); Narang, *Meth. Enzymol.* 68:90 (1979); Brown, *Meth. Enzymol.* 68:109 (1979); Beaucage, *Tetra. Lett.* 22:1859 (1981); U.S. Pat. No. 4,458,066. Double-stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, for example, for generating mutations in sequences, subcloning, labeling probes, sequencing, hybridization and the like are well described in the scientific and patent literature. See, e.g., Sambrook, ed., Molecular Cloning: A Laboratory Manual (2nd ed.), Vols. 1-3, Cold Spring Harbor Laboratory (1989); Ausubel, ed., *Current Protocols in Molecular Biology*, John Wiley & Sons, Inc., New York (1997); Tijssen, ed., *Laboratory Techniques in Biochemistry and Molecular Biology: Hybridization With Nucleic Acid Probes, Part 1, Theory and Nucleic Acid Preparation*, Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g., fluid or gel precipitin reactions, immunodiffusion, immunoelectrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Oligonucleotide primers may be used to amplify nucleic acids encoding a T2R ligand-binding region. The nucleic acids described herein can also be cloned or measured quantitatively using amplification techniques. Amplification methods are also well known in the art, and include, e.g., polymerase chain reaction (PCR) (Innis ed., *PCR Protocols, a Guide to Methods and Applications*, Academic Press, N.Y. (1990); Innis ed., *PCR Strategies*, Academic Press, Inc., N.Y. (1995)), ligase chain reaction (LCR) (Wu, *Genomics,* 4:560 (1989); Landegren, *Science,* 241:1077 (1988); Barringer, *Gene,* 89:117 (1990)); transcription amplification (Kwoh, *PNAS,* 86:1173 (1989)); self-sustained sequence replication (Guatelli, *PNAS,* 87:1874 (1990)); Q Beta replicase amplification (Smith, *J. Clin. Microbiol.*, 35:1477-91 (1997)); automated Q-beta replicase amplification assay (Burg, *Mol. Cell. Probes,* 10:257-71 (1996)); and other RNA polymerase mediated techniques (e.g., NASBA, Cangene, Mississauga, Ontario). See also, Berger, *Methods Enzymol.*, 152:307-16 (1987); Sambrook; Ausubel; U.S. Pat. Nos. 4,683,195 and 4,683,202; Sooknanan, *Biotechnology,* 13:563-64 (1995).

Once amplified, the nucleic acids, either individually or as libraries, may be cloned according to methods known in the art, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" the PCR primer pair. For example, Pst I and Bsp E1 sites were designed into the exemplary primer pairs of the invention. These particular restriction sites have a sequence that, when ligated, are "in-frame" with respect to the 7-membrane receptor "donor" coding sequence into which they are spliced (the ligand-binding region coding sequence is internal to the 7-membrane polypeptide, thus, if it is desired that the construct be translated downstream of a restriction enzyme splice site, out of frame results should be avoided; this may not be necessary if the inserted ligand-binding region comprises substantially most of the transmembrane VII region). The primers can be designed to retain the original sequence of the "donor" 7-membrane receptor. Alternatively, the primers can encode amino acid residues that are conservative substitutions (e.g., hydrophobic for hydrophobic residue, see above discussion) or functionally benign substitutions (e.g., do not prevent plasma membrane insertion, cause cleavage by peptidase, cause abnormal folding of receptor, and the like).

The primer pairs may be designed to selectively amplify ligand-binding regions of T2R proteins. These binding regions may vary for different ligands; thus, what may be a minimal binding region for one ligand, may be too limiting for a second potential ligand. Thus, binding regions of different sizes comprising different domain structures may be amplified; for example, transmembrane (TM) domains II through VII, III through VII, III through VI or II through VI, or variations thereof (e.g. only a subsequence of a particular domain, mixing the order of the domains, and the like), of a 7-transmembrane T2R.

As domain structures and sequence of many 7-membrane T2R proteins are known, the skilled artisan can readily select domain-flanking and internal domain sequences as model sequences to design degenerate amplification primer pairs. For example, a nucleic acid sequence encoding domain regions II through VII can be generated by PCR amplification using a primer pair. To amplify a nucleic acid comprising transmembrane domain I (TM I) sequence, a degenerate primer can be designed from a nucleic acid that encodes the amino acid sequence of the T2R family consensus sequence 1 described above. Such a degenerate primer can be used to generate a binding region incorporating TM I through TM III, TM I through TM IV, TM I through TM V, TM I through TM VI or TM I through TM VII). Other degenerate primers can be designed based on the other T2R family consensus sequences provided herein. Such a degenerate primer can be used to generate a binding region incorporating TM III through TM IV, TM III through TM V, TM III through TM VI or TM III through TM VII.

Paradigms to design degenerate primer pairs are well known in the art. For example, a COnsensus-DEgenerate Hybrid Oligonucleotide Primer (CODEHOP) strategy computer program is accessible and is directly linked from the BlockMaker multiple sequence alignment site for hybrid primer prediction beginning with a set of related protein sequences, as known taste receptor ligand-binding regions (see, e.g. Rose, *Nucleic Acids Res.*, 26:1628-35 (1998); Singh, *Biotechniques*, 24:318-19 (1998)).

Means to synthesize oligonucleotide primer pairs are well known in the art. "Natural" base pairs or synthetic base pairs can be used. For example, use of artificial nucleobases offers a versatile approach to manipulate primer sequence and generate a more complex mixture of amplification products. Various families of artificial nucleobases are capable of assuming multiple hydrogen bonding orientations through internal bond rotations to provide a means for degenerate molecular recognition. Incorporation of these analogs into a single position of a PCR primer allows for generation of a complex library of amplification products. See, e.g., Hoops, *Nucleic Acids Res.*, 25:4866-71 (1997). Nonpolar molecules can also be used to mimic the shape of natural DNA bases. A non-hydrogen-bonding shape mimic for adenine can replicate efficiently and selectively against a nonpolar shape mimic for thymine (see, e.g., Morales, *Nat. Struct. Biol.*, 5:950-54 (1998)). For example, two degenerate bases can be the pyrimidine base 6H, 8H-3,4-dihydropyrimido[4,5-c][1,2]oxazin-7-one or the purine base N6-methoxy-2,6-diaminopurine (see, e.g., Hill, *PNAS*, 95:4258-63 (1998)). Exemplary degenerate primers of the invention incorporate the nucleobase analog 5'-Dimethoxytrityl-N-benzoyl-2'-deoxy-Cytidine,3'-[(2-cyanoethyl)-(N,N-diisopropyl)]-phosphoramidite (the term "P" in the sequences, see above). This pyrimidine analog hydrogen bonds with purines, including A and G residues.

Polymorphic variants, alleles, and interspecies homologs that are substantially identical to a taste receptor disclosed herein can be isolated using the nucleic acid probes described above. Alternatively, expression libraries can be used to clone T2R polypeptides and polymorphic variants, alleles, and interspecies homologs thereof, by detecting expressed homologs immunologically with antisera or purified antibodies made against a T2R polypeptide, which also recognize and selectively bind to the T2R homolog.

Nucleic acids that encode ligand-binding regions of taste receptors may be generated by amplification (e.g., PCR) of appropriate nucleic acid sequences using appropriate (perfect or degenerate) primer pairs. The amplified nucleic acid can be genomic DNA from any cell or tissue or mRNA or cDNA derived from taste receptor-expressing cells.

In one embodiment, hybrid protein-coding sequences comprising nucleic acids encoding T2Rs fused to a translocation sequences may be constructed. Also provided are hybrid T2Rs comprising the translocation motifs and tastant-binding regions of other families of chemosensory receptors, particularly taste receptors. These nucleic acid sequences can be operably linked to transcriptional or translational control elements, e.g., transcription and translation initiation sequences, promoters and enhancers, transcription and translation terminators, polyadenylation sequences, and other sequences useful for transcribing DNA into RNA. In construction of recombinant expression cassettes, vectors, and transgenics, a promoter fragment can be employed to direct expression of the desired nucleic acid in all desired cells or tissues.

In another embodiment, fusion proteins may include C-terminal or N-terminal translocation sequences. Further, fusion proteins can comprise additional elements, e.g., for protein detection, purification, or other applications. Detection and purification facilitating domains include, e.g., metal chelating peptides such as polyhistidine tracts, histidine-tryptophan modules, or other domains that allow purification on immobilized metals; maltose binding protein; protein A domains that allow purification on immobilized immunoglobulin; or the domain utilized in the FLAGS extension/affinity purification system (Immunex Corp, Seattle Wash.).

The inclusion of a cleavable linker sequences such as Factor Xa (see, e.g., Ottavi, Biochimie, 80:289-93 (1998)), subtilisin protease recognition motif (see, e.g., Polyak, *Protein Eng.*, 10:615-19 (1997)); enterokinase (Invitrogen, San Diego, Calif.), and the like, between the translocation domain (for efficient plasma membrane expression) and the rest of the newly translated polypeptide may be useful to facilitate purification. For example, one construct can include a polypeptide encoding a nucleic acid sequence linked to six histidine residues followed by a thioredoxin, an enterokinase cleavage site (see, e.g., Williams, *Biochemistry*, 34:1787-97 (1995)), and an C-terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature (see, e.g., Kroll, *DNA Cell. Biol.*, 12:441-53 (1993)).

Expression vectors, either as individual expression vectors or as libraries of expression vectors, comprising the ligand-binding region encoding sequences may be introduced into a genome or into the cytoplasm or a nucleus of a cell and expressed by a variety of conventional techniques, well described in the scientific and patent literature. See, e.g., Roberts, *Nature*, 328:731 (1987); Berger supra; Schneider, *Protein Expr. Purif.*, 6435:10 (1995); Sambrook; Tijssen; Ausubel. Product information from manufacturers of biological reagents and experimental equipment also provide information regarding known biological methods. The vectors can be isolated from natural sources, obtained from such sources as ATCC or GenBank libraries, or prepared by synthetic or recombinant methods.

The nucleic acids can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, bleomycin, hygromycin) or herbicide resistance (e.g., chlorosulfuron or Basta) to permit selection of those cells transformed with the desired DNA sequences (see, e.g., Blondelet-Rouault, *Gene*, 190:315-17 (1997); Aubrecht, *J. Pharmacol. Exp. Ther.*, 281:992-97 (1997)). Because selectable marker genes conferring resistance to substrates like neomycin or hygromycin can only be utilized in tissue culture, chemoresistance genes are also used as selectable markers in vitro and in vivo.

A chimeric nucleic acid sequence may encode a T2R ligand-binding region within any 7-transmembrane polypeptide. Because 7-transmembrane receptor polypeptides have similar primary sequences and secondary and tertiary structures, structural domains (e.g., extracellular domain, TM domains, cytoplasmic domain, etc.) can be readily identified by sequence analysis. For example, homology modeling, Fourier analysis and helical periodicity detection can identify and characterize the seven domains with a 7-transmembrane receptor sequence. Fast Fourier Transform (FFT) algorithms can be used to assess the dominant periods that characterize profiles of the hydrophobicity and variability of analyzed sequences. Periodicity detection enhancement and alpha helical periodicity index can be done as by, e.g., Donnelly, *Protein Sci.*, 2:55-70 (1993). Other alignment and modeling algorithms are well known in the art (see, e.g., Peitsch, *Receptors Channels*, 4:161-64 (1996); Kyte & Doolittle, *J. Md. Biol.*, 157:105-32 (1982); Cronet, *Protein Eng.*, 6:59-64 (1993); http://bioinfo.weizmann.ac.il/).

The present invention also includes not only the nucleic acid molecules and polypeptides having the specified nucleic and amino acid sequences, but also fragments thereof, particularly fragments of, e.g., 40, 60, 80, 100, 150, 200, or 250 nucleotides, or more, as well as polypeptide fragments of, e.g., 10, 20, 30, 50, 70, 100, or 150 amino acids, or more. Optionally, the nucleic acid fragments can encode an antigenic polypeptide that is capable of binding to an antibody raised against a T2R family member. Further, a protein fragment of the invention can optionally be an antigenic fragment that is capable of binding to an antibody raised against a T2R family member.

Also contemplated are chimeric proteins, comprising at least 10, 20, 30, 50, 70, 100, or 150 amino acids, or more, of one of at least one of the T2R polypeptides described herein, coupled to additional amino acids representing all or part of another GPCR, preferably a member of the 7 transmembrane superfamily. These chimeras can be made from the instant receptors and another GPCR, or they can be made by combining two or more of the present receptors. In one embodiment, one portion of the chimera corresponds to, or is derived from the transmembrane domain of a T2R polypeptide of the invention. In another embodiment, one portion of the chimera corresponds to, or is derived from the one or more of the transmembrane regions of a T2R polypeptide described herein, and the remaining portion or portions can come from another GPCR. Chimeric receptors are well known in the art, and the techniques for creating them and the selection and boundaries of domains or fragments of G Protein-Coupled Receptors for incorporation therein are also well known. Thus, this knowledge of those skilled in the art can readily be used to create such chimeric receptors. The use of such chimeric receptors can provide, for example, a taste selectivity characteristic of one of the receptors specifically disclosed herein, coupled with the signal transduction characteristics of another receptor, such as a well known receptor used in prior art assay systems.

For example, a region such as a ligand-binding region, an extracellular domain, a transmembrane domain, a transmembrane domain, a cytoplasmic domain, an N-terminal domain, a C terminal domain, or any combination thereof, can be covalently linked to a heterologous protein. For instance, a T2R transmembrane region can be linked to a heterologous GPCR transmembrane domain, or a heterologous GPCR extracellular domain can be linked to a T2R transmembrane region. Other heterologous proteins of choice can include, e.g., green fluorescent protein, β-gal, glutamtate receptor, and the rhodopsin N-terminus.

Also within the scope of the invention are host cells for expressing the T2Rs, fragments, or variants of the invention. To obtain high levels of expression of a cloned gene or nucleic acid, such as cDNAs encoding the T2Rs, fragments, or variants of the invention, one of skill typically subclones the nucleic acid sequence of interest into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. However, bacterial or eukaryotic expression systems can be used.

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al.) It is only necessary that the particular genetic engineering procedure used be capable of successfully introducing at lest one nucleic acid molecule into the host cell capable of expressing the T2R, fragment, or variant of interest.

After the expression vector is introduced into the cells, the transfected cells are cultured under conditions favoring expression of the receptor, fragment, or variant of interest, which is then recovered from the culture using standard techniques. Examples of such techniques are well known in the art. See, e.g., WO 00/06593, which is incorporated by reference in a manner consistent with this disclosure.

D. Immunological Detection of T2Rs

In addition to the detection of T2R genes and gene expression using nucleic acid hybridization technology, one can also use immunoassays to detect T2Rs, e.g., to identify taste receptor cells, and variants of T2R family members. Immunoassays can be used to qualitatively or quantitatively analyze the T2Rs. A general overview of the applicable technology can be found in Harlow & Lane, *Antibodies: A Laboratory Manual* (1988).

1. Antibodies to T2R Family Members

Methods of producing polyclonal and monoclonal antibodies that react specifically with a T2R family member are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature*, 256:495-97 (1975)). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science*, 246:1275-81 (1989); Ward et al., *Nature*, 341:544-46 (1989)).

A number of T2R-comprising immunogens may be used to produce antibodies specifically reactive with a T2R family member. For example, a recombinant T2R protein, or an antigenic fragment thereof can be isolated as described herein. Suitable antigenic regions include, e.g., the consensus sequences disclosed above that can be used to identify members of the T2R family. Recombinant proteins can be expressed in eukaryotic or prokaryotic cells as described above, and purified as generally known in the art. Recombinant protein is a preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product may then be injected into an animal capable of producing antibodies. Either monoclonal or polyclonal antibodies may be generated, for subsequent use in immunoassays to measure the protein.

More specifically, methods of production of polyclonal antibodies are known to those of skill in the art. For example, an inbred strain of mice (e.g. BALB/C mice) or rabbits may be immunized with a T2R polypeptide using a standard adjuvant, such as Freund's adjuvant, and a standard immunization protocol. The animal's immune response to the immunogen preparation may then be monitored by taking test bleeds and determining the titer of reactivity to the T2R. When appropriately high titers of antibody to the immunogen are obtained, blood may be collected from the animal and antisera may be prepared. Further fractionation of the antisera to enrich for antibodies reactive to the T2R polypeptide can be done if desired (see Harlow & Lane, supra).

Monoclonal antibodies may be obtained by various techniques familiar to those skilled in the art. Briefly, spleen cells from an animal immunized with a desired antigen may be immortalized, commonly by fusion with a myeloma cell (see Kohler & Milstein, *Eur. J. Immunol*, 6:511-19 (1976)). Alternative methods of immortalization include transformation with Epstein Barr Virus, oncogenes, retroviruses, or other methods well known in the art. Colonies arising from single immortalized cells may then be screened for production of antibodies of the desired specificity and affinity for the antigen. Yield of the monoclonal antibodies produced by such cells may be enhanced by various techniques, including injection into the peritoneal cavity of a vertebrate host. Alternatively, one may isolate nucleic acid sequences that encode a monoclonal antibody, or a binding fragment thereof, by screening a nucleic acid library from human B cells according to the general protocol outlined by Huse et al., *Science,* 246: 1275-81 (1989).

Monoclonal antibodies and polyclonal sera are generally collected and titered against the immunogen protein in an immunoassay, e.g., a solid phase immunoassay with the immunogen immobilized on a solid support. Typically, polyclonal antisera with a titer of 104 or greater may be selected and tested for their cross reactivity against non-T2R proteins, or even other T2R family members or other related proteins from other organisms, using a competitive binding immunoassay. Specific polyclonal antisera and monoclonal antibodies will usually bind with a Kd of at least about 0.1 mM, more usually at least about 1 pM, optionally at least about 0.1 pM or better, and optionally 0.01 pM or better.

Once T2R family member specific antibodies are available, individual T2R proteins can be detected by a variety of immunoassay methods. For a review of immunological and immunoassay procedures, see Stites & Terr eds., *Basic and Clinical Immunology* (7th ed. 1991). Moreover, the immunoassays of the present invention can be performed in any of several configurations, which are reviewed extensively in Maggio, ed., *Enzyme Immunoassay* (1980); and Harlow & Lane, supra.

2. Immunological Binding Assays

T2R proteins can be detected and/or quantified using any of a number of well recognized immunological binding assays (see, e.g., U.S. Pat. Nos. 4,366,241; 4,376,110; 4,517,288; and 4,837,168). For a review of the general immunoassays, see Asai, ed., *Methods in Cell Biology: Antibodies in Cell Biology*, volume 37 (1993); Stites & Terr, eds., *Basic and Clinical Immunology* (7th ed. 1991). Immunological binding assays (or immunoassays) typically use an antibody that specifically binds to a protein or antigen of choice (in this case a T2R family member or an antigenic subsequence thereof). The antibody (e.g., anti-T2R) may be produced by any of a number of means well known to those of skill in the art, as described above.

Immunoassays also often use a labeling agent to specifically bind to, and label the complex formed by the antibody and antigen. The labeling agent may itself be one of the moieties comprising the antibody/antigen complex. Thus, the labeling agent may be a labeled T2R polypeptide or a labeled anti-T2R antibody. Alternatively, the labeling agent may be a third moiety, e.g., a secondary antibody, that specifically binds to the antibody/T2R complex. (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.,* 111:1401-06 (1973); Akerstrom et al., *J. Immunol.,* 135:2589-642 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will generally depend upon the assay format, antigen, volume of solution, concentrations, and the like. Usually, the assays will be carried out at ambient temperature, although they can be conducted over a range of temperatures, e.g., from about 10° C. to about 40° C.

a. Non-Competitive Assay Formats

Immunoassays for detecting a T2R protein in a sample may be either competitive or noncompetitive. Noncompetitive immunoassays are assays in which the amount of antigen is directly measured. In one preferred "sandwich" assay, for example, the anti-T2R antibodies can be bound directly to a solid substrate on which they are immobilized. These immobilized antibodies may then capture any T2R protein present in the test sample. The T2R protein is thus immobilized, and is then bound by a labeling agent, such as a second T2R antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

b. Competitive Assay Formats

In competitive assays, the amount of T2R protein present in the sample is measured indirectly by measuring the amount of a known, added (exogenous) T2R protein displaced (competed away) from an anti-T2R antibody by the unknown T2R protein present in a sample. In one competitive assay, a known amount of T2R protein is added to a sample, and the sample is then contacted with an antibody that specifically binds to the T2R. The amount of exogenous T2R protein bound to the antibody is inversely proportional to the concentration of T2R protein present in the sample. In a particularly preferred embodiment, the antibody is immobilized on a solid substrate. The amount of T2R protein bound to the antibody may be determined either by measuring the amount of T2R protein present in a T2R/antibody complex, or alternatively by measuring the amount of remaining uncomplexed protein. The amount of T2R protein may be detected by providing a labeled T2R molecule.

A hapten inhibition assay is another preferred competitive assay. In this assay the known T2R protein is immobilized on a solid substrate. A known amount of anti-T2R antibody is added to the sample, and the sample is then contacted with the immobilized T2R. The amount of anti-T2R antibody bound to the known immobilized T2R protein is inversely proportional to the amount of T2R protein present in the sample. Again, the amount of immobilized antibody may be detected by detecting either the immobilized fraction of antibody or the fraction of the antibody that remains in solution. Detection may be direct where the antibody is labeled, or indirect by the subsequent addition of a labeled moiety that specifically binds to the antibody as described above.

c. Cross-reactivity Determinations

Immunoassays in the competitive binding format can also be used for cross-reactivity determinations. For example, a protein at least partially encoded by the nucleic acid sequences disclosed herein can be immobilized to a solid support. Proteins (e.g., T2R polypeptides and homologs thereof) may be added to the assay and thereby compete for binding of the antisera to the immobilized antigen. The ability of the added proteins to compete for binding of the antisera to the immobilized protein is compared to the ability of the T2R polypeptide encoded by the nucleic acid sequences disclosed herein to compete with itself. The percent cross-reactivity for the above proteins is calculated, using standard calculations. Those antisera with less than 10% cross-reactivity with each of the added proteins listed above are selected and pooled. The cross-reacting antibodies are optionally removed from the pooled antisera by immunoabsorption with the added considered proteins, e.g., distantly related homologs. In addition, peptides comprising amino acid sequences representing consensus sequences that may be used to identify members of the T2R family can be used in cross-reactivity determinations.

The immunoabsorbed and pooled antisera may then be used in a competitive binding immunoassay as described above to compare a second protein, thought to be perhaps an allele or polymorphic variant of a T2R family member, to the immunogen protein (i.e., T2R protein encoded by the nucleic acid sequences disclosed herein). In order to make this comparison, the two proteins are each assayed at a wide range of concentrations and the amount of each protein required to inhibit 50% of the binding of the antisera to the imobilized protein is determined. If the amount of the second protein required to inhibit 50% of binding is less than 10 times the amount of the protein encoded by nucleic acid sequences disclosed herein required to inhibit 50% of binding, then the second protein is said to specifically bind to the pblyclonal antibodies generated to a T2R immunogen.

Antibodies raised against T2R consensus sequences can also be used to prepare antibodies that specifically bind only to GPCRs of the T2R family, but not to GPCRs from other families. For example, polyclonal antibodies that specifically bind to a particular member of the T2R family can be made by subtracting out cross-reactive antibodies using other T2R family members Species-specific polyclonal antibodies can be made in a similar way. For example, antibodies specific to human T2R1 can be made by, subtracting out antibodies that are cross-reactive with orthologous sequences, e.g., rat T2R1 or mouse T2R1.

d. Other Assay Formats

Western blot (immunoblot) analysis may be used to detect and quantify the presence of T2R protein in a sample. The technique generally comprises separating sample proteins by gel electrophoresis on the basis of molecular weight, transferring the separated proteins to a suitable solid support, (e.g. a nitrocellulose filter, a nylon filter, or derivatized nylon filter), and incubating the sample with antibodies that specifically bind the T2R protein. The anti-T2R polypeptide antibodies then specifically bind to the T2R polypeptide on the solid support. These antibodies may be directly labeled, or alternatively may be subsequently detected using labeled antibodies (e.g., labeled sheep anti-mouse antibodies) that specifically bind to the anti-T2R antibodies.

Other, assay formats include liposome immunoassays (LIA), which use liposomes designed to bind specific molecules (e.g., antibodies) and release encapsulated reagents or markers. The released chemicals are then detected according to standard techniques (see Monroe et al., Amer. Clin. Prod. Rev., 5:34-41 (1986)).

e. Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, these techniques involve coating the substrate with a proteinaceous composition. In particular, protein compositions such as bovine serum albumin (BSA), nonfat powdered milk, and gelatin are widely used, with powdered milk being most preferred.

f. Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well developed in the field of immunoassays and, in general, most any label useful in such methods can be applied to the present invention. Thus, a label is any composition detectable by spectroscopic, photochemical, biochemical, immunochemical, electrical, optical, or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, $^{32}$P), enzymes (e.g., horseradish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize a T2R protein, or secondary antibodies that recognize anti-T2R.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, e.g., where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge-coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen coated particles are agglutinated by samples comprising the target antibodies. In this format, none of the components need be labeled and the presence of the target antibody is detected by simple visual inspection.

E. Detection of Taste Modulators

Methods and compositions for determining whether a test compound specifically binds to a T2R polypeptide of the invention, both in vitro and in vivo are described below. Many aspects of cell physiology can be monitored to assess the effect of ligand-binding to a naturally occurring or chimeric T2Rs. These assays may be performed on intact cells expressing a T2R polypeptide, on permeabilized cells, or on membrane fractions produced by standard methods.

Taste receptors bind tastants and initiate the transduction of chemical stimuli into electrical signals. An activated or inhibited G Protein will in turn alter the properties of target enzymes, channels, and other effector proteins. Some examples are the activation of cGMP phosphodiesterase by transducin in the visual system, adenylate cyclase by the stimulatory G Protein, phospholipase C by Gq and other cognate G Proteins, and modulation of diverse channels by Gi and other G Proteins. Downstream consequences can also be examined such as generation of diacyl glycerol and IP3 by phospholipase C, and in turn, for calcium mobilization by IP3.

The T2R proteins or polypeptides of the assay will typically be selected from a polypeptide having a sequence of SEQ ID NOS: 2, 4, 6, 8, 10, 12, 14, 16, 18, 20, and 24, or fragments or conservatively modified variants thereof.

Alternatively, the T2R proteins of polypeptides of the assay can be derived from a eukaryote host cell, and can include an amino acid subsequence having amino acid sequence identity to SEQ ID NOS: 2, 4, 6, 8, 10, 12, 14, 16, 18, 20, and 24, or conservatively modified variants thereof. Generally, the amino acid sequence identity will be at least 30% preferably 30-40%, more specifically 50-60, 70%, 75%; 80%, 85%, 90%, 95%, 96%, 97%, 98%, or 99%. Optionally, the T2R proteins or polypeptides of the assays can comprise a region of a T2R polypeptide, such as an extracellular domain, transmembrane region, cytoplasmic domain, ligand-binding domain, and the like. Optionally, the T2R polypeptide, or a portion thereof, can be covalently linked to a heterologous protein to create a chimeric protein used in the assays described herein.

Modulators of T2R activity may be tested using T2R proteins or polypeptides as described above, either recombinant or naturally occurring. The T2R proteins or polypeptides can be isolated, expressed in a cell, expressed in a membrane derived from a cell, expressed in tissue or in an animal, either recombinant or naturally occurring. For example, tongue slices, dissociated cells from a tongue, transformed cells, or membranes can be used. Modulation can be tested using one of the in vitro or in vivo assays described herein.

1. In Vitro Binding Assays

Taste transduction can also be examined in vitro with soluble or solid state reactions, using a T2R polypeptide or a chimeric molecule, such as an extracellular domain, transmembrane region, or combination thereof, of a T2R covalently linked to a heterologous signal transduction domain; or a heterologous extracellular domain and/or transmembrane region covalently linked to the transmembrane and/or cytoplasmic domain of a T2R protein or polypeptide. Furthermore, ligand-binding regions of a T2R polypeptide can be used in vitro in soluble or solid state reactions to assay for ligand binding. In numerous embodiments, a chimeric receptor can be made that comprises all or part of a T2R polypeptide, as well an additional sequence that facilitates the localization of the T2R to the membrane, such as a rhodopsin, e.g., an N-terminal fragment of a rhodopsin protein.

Ligand binding to a T2R protein, a ligand-binding region, or chimeric protein can be tested in solution, in a bilayer membrane, attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties.

T2R-G Protein interactions can also be examined. For example, binding of the G Protein to the T2R polypeptide or its release from the polypeptide can be examined. In the absence of GTP, an activator will lead to the formation of a tight complex of a G protein (all three subunits) with the T2R. This complex can be detected in a variety of ways, as noted above. Such an assay can be modified to search for inhibitors, e.g., by adding an activator to the T2R and G protein in the absence of GTP, which form a tight complex, and then screen for inhibitors by looking at dissociation of the T2R-G protein complex. In the presence of GTP, release of the alpha subunit of the G protein from the other two G protein subunits serves as a criterion of activation.

In another embodiment of the invention, a GTPγS assay may be used. As described above, upon activation of a GPCR, the Gα subunit of the G protein complex is stimulated to exchange bound GDP for GTP. Ligand-mediated stimulation of G protein exchange activity can be measured in a biochemical assay measuring the binding of added radioactively-labeled GTPγ$^{35}$S to the G protein in the presence of a putative ligand. Typically, membranes containing the chemosensory receptor of interest are mixed with a complex of G proteins. Potential inhibitors and/or activators and GTPγS are added to the assay, and binding of GTPγS to the G protein is measured. Binding can be measured by liquid scintillation counting or by any other means known in the art, including scintillation proximity assays (SPA). In other assays formats, fluorescently-labeled GTPγS can be utilized.

In particularly preferred embodiments, T2R-gustducin interactions may be monitored as a function of T2R receptor activation. For instance, mouse T2R5 shows strong cycloheximide dependent coupling with gustducin. Such ligand dependent coupling of T2R receptors with gustducin can be used as a marker to identify modifiers of any member of the T2R family.

2. Fluorescence Polarization Assays

In another embodiment, Fluorescence Polarization ("FP") based assays may be used to detect and monitor ligand binding. Fluorescence polarization is a versatile laboratory technique for measuring equilibrium binding, nucleic acid hybridization, and enzymatic activity. Fluorescence polarization assays are homogeneous in that they do not require a separation step such as centrifugation, filtration, chromatography, precipitation, or electrophoresis. These assays are done in real time, directly in solution and do not require an immobilized phase. Polarization values can be measured repeatedly and after the addition of reagents since measuring the polarization is rapid and does not destroy the sample. Generally, this technique can be used to measure polarization values of fluorophores from low picomolar to micromolar levels. This section describes how fluorescence polarization can be used in a simple and quantitative way to measure the binding of ligands to the T2R polypeptides of the invention.

When a fluorescently labeled molecule is excited with plane polarized light, it emits light that has a degree of polarization that is inversely proportional to its molecular rotation. Large fluorescently labeled molecules remain relatively stationary during the excited state (4 nanoseconds in the case of fluorescein) and the polarization of the light remains relatively constant between excitation and emission. Small fluorescently labeled molecules rotate rapidly during the excited state and the polarization changes significantly between excitation and emission. Therefore, small molecules have low polarization values and large molecules have high polarization values. For example, a single-stranded fluorescein-labeled oligonucleotide has a relatively low polarization value but when it is hybridized to a complementary strand, it has a higher polarization value. When using FP to detect and monitor tastant-binding which may activate or inhibit the chemosensory receptors of the invention, fluorescence-labeled tastants or auto-fluorescent tastants may be used.

Fluorescence polarization (P) is defined as:

$$P = \frac{Int_{\parallel} - Int_{\perp}}{Int_{\parallel} + Int_{\perp}}$$

Where $\parallel$ is the intensity of the emission light parallel to the excitation light plane and Int $\perp$ is the intensity of the emission light perpendicular to the excitation light plane. P, being a ratio of light intensities, is a dimensionless number. For example, the Beacon® and Beacon 2000™ System may be used in connection with these assays. Such systems typically express polarization in millipolarization units (1 Polarization Unit=1000 mP Units).

The relationship between molecular rotation and size is described by the Perrin equation. Summarily, the Perrin equation states that polarization is directly proportional to the rotational relaxation time, the time that it takes a molecule to rotate through an angle of approximately 68.5° Rotational relaxation time is related to viscosity ($\eta$), absolute temperature (T), molecular volume (V), and the gas constant to (R) by the following equation:

$$RotationalRelaxionTime = \frac{3\eta V}{RT}$$

The rotational relaxation time is small ($\approx 1$ nanosecond) for small molecules (e.g. fluorescein) and large ($\approx 100$ nanoseconds) for large molecules (e.g. immunoglobulins). If viscosity and temperature are held constant, rotational relaxation time, and therefore polarization, is directly related to the molecular volume. Changes in molecular volume may be due to interactions with other molecules, dissociation, polymerization, degradation, hybridization, or conformational changes of the fluorescently labeled molecule. For example, fluorescence polarization has been used to measure enzymatic cleavage of large fluorescein labeled polymers by proteases, DNases, and RNases. It also has been used to measure equilibrium binding for protein/protein interactions, antibody/antigen binding, and protein/DNA binding.

3. Solid State and Soluble High Throughput Assays

In yet another embodiment, the invention provides soluble assays using a T2R polypeptide; or a cell or tissue expressing a T2R polypeptide. In another embodiment, the invention provides solid phase based in vitro assays in a high throughput format, where the T2R polypeptide, or cell or tissue expressing the T2R polypeptide is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 1000 to about 1500 different compounds. It is also possible to assay multiple compounds in each plate well. Further, it is possible to assay several different plates per day allowing for assay screens of about 6,000-20,000 compounds per day. More recently, microfluidic approaches to reagent manipulation have been developed.

The molecule of interest can be bound to the solid state component, directly or indirectly, via covalent or non-covalent linkage, e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein A, it can be used in conjunction with appropriate tag binders (avidin, streptavidin, neutravidin, the Fc region of an immunoglobulin, etc.) Antibodies to molecules with natural binders such as biotin are also widely available and appropriate tag binders (see, SIGMA Immunochemicals 1998 catalogue, SIGMA, St. Louis Mo.).

Similarly, any haptenic or antigenic compound can be used in combination with an appropriate antibody to form a tag/tag binder pair Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, e.g., polyurethanes, polyesters, polycarbonates, polyureas, polyamides, polyethyleneimines, polyarylene sulfides, polysiloxanes, polyimides, and polyacetates, can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders may be fixed to solid substrates using any of a variety of methods currently available. Solid substrates are commonly derivatized or functionalized by exposing all or a portion of the substrate to a chemical reagent which fixes a chemical group to the surface that is reactive with a portion of the tag binder. For example, groups that are suitable for attachment to a longer chain portion include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.*, 85:2149-54 (1963) (describing solid phase synthesis of, e.g., peptides); Geysen et al., *Immun. Meth.*, 102:259-74 (1987) (describing synthesis of solid phase components on pins); Frank & Doring, *Tetrahedron*, 44:60316040 (1988) (describing synthesis of various peptide sequences on cellulose disks); Fodor et al., *Science*, 251:767-77 (1991); Sheldon et al., *Clinical Chemistry*, 39(4); 718-19 (1993); and Kozal et al., *Nature Medicine*, 2(7):753759 (1996) (all describing arrays of biopolymers fixed to solid substrates). Non-chemical approaches for fixing tag binders to substrates include other common methods, such as heat, cross-linking by UV radiation, and the like.

4. Computer-Based Assays

Yet another assay for compounds that modulate T2R polypeptide activity involves computer assisted compound design, in which a computer system is used to generate a three-dimensional structure of an T2R polypeptide based on the structural information encoded by its amino acid sequence. The input amino acid sequence interacts directly and actively with a preestablished algorithm in a computer program to yield secondary, tertiary, and quaternary structural models of the protein. The models of the protein structure are then examined to identify regions of the structure that have the ability to bind, e.g., ligands. These regions are then used to identify ligands that bind to the protein.

The three-dimensional structural model of the protein is generated by entering protein amino acid sequences of at least 10 amino acid residues or corresponding nucleic acid sequences encoding a T2R polypeptide into the computer system. The nucleotide sequence encoding the T2R polypeptide, or the amino acid sequence-thereof can be any sequence disclosed herein, and conservatively modified versions thereof.

The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand-binding regions are identified by the computer system. Three-dimensional structures for potential ligands are generated by entering amino acid or nucleotide sequences or chemical formulas of compounds, as described above. The three-dimensional structure of the potential ligand is then compared to that of the T2R polypeptide to identify ligands that bind to the protein. Binding affinity between the protein and ligands is determined using energy terms to determine which ligands have an enhanced probability of binding to the protein.

Computer systems are also used to screen for mutations, polymorphic variants, alleles, and interspecies homologs of T2R genes. Such mutations can be associated with disease states or genetic traits. As described above, GeneChip™ and related technology can also be used to screen for mutations, polymorphic variants, alleles, and interspecies homologs. Once the variants are identified, diagnostic assays can be used to identify patients having such mutated genes. Identification of the mutated T2R genes involves receiving input of a first nucleic acid or amino acid sequence of a T2R gene, or conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in various T2R genes, and mutations associated with disease states and genetic traits.

5. Cell-Based Binding Assays

In a preferred embodiment, a T2R protein or polypeptide is expressed in a eukaryotic cell as a chimeric receptor with a heterologous, chaperone sequence that facilitates its maturation and targeting through the secretory pathway. In a preferred embodiment, the heterologous sequence is a rhodopsin sequence, such as an N-terminal fragment of a rhodopsin. Such chimeric T2R proteins can be expressed in any eukaryotic cell, such as HEK-293 cells. Preferably, the cells comprise a functional G Protein, e.g., Gα15, that is capable of coupling the chimeric receptor to an intracellular signaling pathway or to a signaling protein such as phospholipase C. Activation of such chimeric receptors in such cells can be detected using any standard method, such as by detecting changes in intracellular calcium by detecting FURA-2 dependent fluorescence in the cell.

Activated GPCR receptors become substrates for kinases that phosphorylate the C-terminal tail of the receptor (and possibly other sites as well). Thus, activators will promote the transfer of $^{32}P$ from gamma-labeled GTP to the receptor, which can be assayed with a scintillation counter. The phosphorylation of the C-terminal tail will promote the binding of arrestin-like proteins, and will interfere with the binding of G Proteins. The kinase/arrestin pathway plays a key role in the desensitization of many GPCRs. For example, compounds that modulate the duration a taste receptor stays active may be useful as a means of prolonging a desired taste or cutting off an unpleasant one. For a general review of GPCR signal transduction and methods of assaying signal transduction, see, e.g., Methods in Enzymology, vols. 237 and 238 (1994) and volume 96 (1983); Bourne et al., Nature, 10:349:117-27 (1991); Bourne et al., Nature, 348:125-32 (1990); Pitcher et al., Annu. Rev. Biochem., 67:653-92 (1998).

T2R modulation may be assayed by comparing the response of a T2R polypeptide treated with a putative T2R modulator to the response of an untreated control sample. Such putative T2R modulators can include tastants that either inhibit or activate T2R polypeptide activity. In one embodiment, control samples (untreated with activators or inhibitors) are assigned a relative T2R activity value of 100. Inhibition of a T2R polypeptide is achieved when the T2R activity value relative to the control is about 90%, optionally 50% or 25-0%. Activation of a T2R polypeptide is achieved when the T2R activity value relative to the control is 110%, optionally 150%, 200-500%, or 1000-2000%.

Changes in ion flux may be assessed by determining changes in ionic polarization (i.e., electrical potential) of the cell or membrane expressing a T2R polypeptide. One means to determine changes in cellular polarization is by measuring changes in current (thereby measuring changes in polarization) with voltage-clamp and patch-clamp techniques (see, e.g., the "cell-attached" mode, the "inside-out" mode, and the "whole cell" mode, e.g., Ackerman et al., New Engl. J. Med., 336:1575-95 (1997)). Whole cell currents are conveniently determined using known standards. Other known assays include: radiolabeled ion flux assays and fluorescence assays using voltage-sensitive dyes (see, e.g., Vestergarrd-Bogind et al., J. Membrane Biol., 88:67-75 (1988); Gonzales & Tsien, Chem. Biol., 4:269-77 (1997); Daniel et al., J. Pharmacol. Meth., 25:185-93 (1991); Holevinsky et al., J. Membrane Biology, 137:59-70 (1994)). Generally, the compounds to be tested are present in the range from 1 pM to 100 mM.

The effects of test compounds upon the function of the T2R polypeptides can be measured by examining any of the parameters described above. Any suitable physiological change that affects GPCR activity can be used to assess the influence of a test compound on the T2R polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, IP3, cGMP, or cAMP.

Preferred assays for GPCRs include cells that are loaded with ion or voltage sensitive dyes to report receptor activity. Assays for determining activity of such receptors can also use known agonists and antagonists for other G Protein-Coupled Receptors as negative or positive controls to assess activity of tested compounds. In assays for identifying modulatory compounds (e.g., agonists, antagonists), changes in the level of ions in the cytoplasm or membrane voltage may be monitored using an ion sensitive or membrane voltage fluorescent indicator, respectively. Among the ion-sensitive indicators and voltage probes that may be employed are those disclosed in the Molecular Probes 1997 Catalog. For GPCRs, promiscuous G proteins such as Gα15 and Gα16 can be used in the assay of choice (Wilkie et al, PNAS, 88:10049-53 (1991)). Such promiscuous G proteins allow coupling of a wide range of receptors.

Receptor activation typically initiates subsequent intracellular events, e.g., increases in second messengers such as IP3, which releases intracellular stores of calcium ions. Activation of some GPCRs stimulates the formation of inositol triphosphate (IP3) through phospholipase C-mediated hydrolysis of phosphatidylinositol (Berridge & Irvine, Nature, 312:315-21 (1984)). IP3 in turn stimulates the release of intracellular calcium ion stores. Thus, a change in cytoplasmic calcium ion levels, or a change in second messenger levels such as IP3 can be used to assess GPCR function. Cells expressing such GPCRs may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as ECTA, to distinguish fluorescence response resulting from calcium release from internal stores.

Other assays can involve determining the activity of receptors which, when activated, result in a change in the level of intracellular cyclic nucleotides, e.g., cAMP or cGMP, by activating or inhibiting enzymes such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., PNAS, 88:9868-72 (1991); Dhallan et al., Nature, 347:184-87 (1990)). In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-crated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In a preferred embodiment, T2R polypeptide activity is measured by expressing a T2R gene in a heterologous cell with a promiscuous G protein that links the receptor to a phospholipase C signal transduction pathway (see Offermanns & Simon, J. Biol. Chem., 270:15175-80 (1995)). Optionally the cell line is HEK-293 (which does not naturally express T2R genes) and the promiscuous G protein is Gα15 (Offermanns & Simon, supra). Modulation of taste transduction may be assayed by measuring changes in intracellular $Ca^{2+}$ levels, which change in response to modulation of the T2R signal transduction pathway via administration of a molecule that associates with a T2R polypeptide. Changes in $Ca^{2+}$ levels are optionally measured using fluorescent $Ca^{2+}$ indicator dyes and fluorometric imaging.

In one embodiment, the changes in intracellular cAMP or cGMP can be measured using immunoassays. The method described in Offermanns & Simon, *J. Bio. Chem.*, 270:15175-180 (1995), may be used to determine the level of cAMP. Also, the method described in Felley-Bosco et al., *Am. J. Resp. Cell and Mol, Biol.*, 11:159-64 (1994), may be used to determine the level of cGMP. Further, an assay kit for measuring cAMP and/or cGMP is described in U.S. Pat. No. 4,115,538, herein incorporated by reference.

In another embodiment, phosphatidyl inositol (PI) hydrolysis can be analyzed according to U.S. Pat. No. 5,436,128, herein incorporated by reference. Briefly, the assay involves labeling of cells with $^3$H-myoinositol for 48 or more hrs. The labeled cells are treated with a test compound for one hour. The treated cells are lysed and extracted in chloroform-methanol-water, after which the inositol phosphates are separated by ion exchange chromatography and quantified by scintillation counting. Fold stimulation is determined by calculating the ratio of cpm in the presence of agonist, to cpm in the presence of buffer control. Likewise, fold inhibition is determined by calculating the ratio of cpm in the presence of antagonist, to cpm in the presence of buffer control (which may or may not contain an agonist).

In another embodiment, transcription levels can be measured to assess the effects of a test compound on signal transduction. A host cell containing a T2R polypeptide may be contacted with a test compound for a sufficient time to effect any interactions, and then the level of gene expression of a protein of interest is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter gene may be used as described in U.S. Pat. No. 5,436,128, herein incorporated by reference. The reporter genes can be, e.g., chloramphenicol acetyltransferase, luciferase, '3-galactosidase and alkaline phosphatase. Furthermore, the protein of interest can be used as an indirect reporter via attachment to a second reporter such as green fluorescent protein (see, e.g., Mistili & Spector, *Nature Biotechnology*, 15:961-64 (1997)).

The amount of transcription is then compared to the amount of transcription in either the same cell in the absence of the test compound, or it may be compared with the amount of transcription in a substantially identical cell that lacks the T2R polypeptide. A substantially identical cell may be derived from the same cells from which the recombinant cell was prepared but which had not been modified by introduction of heterologous DNA. Any difference in the amount of transcription indicates that the test compound has in some manner altered the activity of the T2R polypeptide of interest.

6. Transgenic Non-human Animals Expressing Taste Receptors

Non-human animals expressing one or more T2R polypeptides of the invention, can also be used for assays. Such expression can be used to determine whether a test compound specifically binds to a mammalian T2R polypeptide in vivo by contacting a non-human animal stably or transiently transfected with a nucleic acid encoding a T2R polypeptide or ligand-binding region thereof with a test compound, and determining whether the animal reacts to the test compound by specifically binding to the polypeptide.

Animals transfected or infected with the vectors of the invention are particularly useful for assays to identify and characterize tastants/ligands that can bind to a specific or sets of receptors. Such vector-infected animals expressing human chemosensory receptor sequences can be used for in vivo screening of tastants and their effect on, e.g., cell physiology (e.g., on taste neurons), on the CNS, or behavior.

Means to infect/express the nucleic acids and vectors, either individually or as libraries, are well known in the art. A variety of individual cell, organ, or whole animal parameters can be measured by a variety of means. The T2R sequences of the invention can be for example expressed in animal taste tissues by delivery with an infecting agent, e.g., adenovirus expression vector.

The endogenous chemosensory receptor genes can remain functional and wild-type (native) activity can still be present. In other situations, where it is desirable that all chemosensory receptor activity is by the introduced exogenous hybrid receptor, use of a knockout line is preferred. Methods for the construction of non-human transgenic animals, particularly transgenic mice, and the selection and preparation of recombinant constructs for generating transformed cells are well known in the art.

Construction of a "knockout" cell and animal is based on the premise that the level of expression of a particular gene in a mammalian cell can be decreased or completely abrogated by introducing into the genome a new DNA sequence that serves to interrupt some portion of the DNA sequence of the gene to be suppressed. Also, "gene trap insertion" can be used to disrupt a host gene, and mouse embryonic stem (ES) cells can be used to produce knockout transgenic animals (see, e.g., Holzschu, *Transgenic Res,* 6:97-106 (1997)). The insertion of the exogenous is typically by homologous recombination between complementary nucleic acid sequences. The exogenous sequence is some portion of the target gene to be modified, such as exonic, intronic or transcriptional regulatory sequences, or any genomic sequence which is able to affect the level of the target gene's expression; or a combination thereof. Gene targeting via homologous recombination in pluripotential embryonic stem cells allows one to modify precisely the genomic sequence of interest. Any technique can be used to create, screen for, propagate, a knockout animal, e.g., see Bijvoet, *Hum. Mol. Genet.*, 7:53-62 (1998); Moreadith, *J. Mol. Med.*, 75:208-16 (1997); Tojo, *Cytotechnology* 19:161-165 (1995); Mudgett, *Methods Mol. Biol.* 48:167-184 (1995); Longo, *Transgenic Res.* 6:321-328 (1997); U.S. Pat. Nos. 5,616,491; 5,464,764; 5,631,153; 5,487,992; 5,627,059; 5,272,071; WO 91/09955; WO93/09222; WO 96/29411; WO 95/31560; WO 91/12650.

The nucleic acids of the invention can also be used as reagents to produce "knockout" human cells and their progeny. Likewise, the nucleic acids of the invention can also be used as reagents to produce "knock-ins" in mice. The human or rat T2R gene sequences can replace the orthologous T2R in the mouse genome. In this way, a mouse expressing a human or rat T2R is produced. This mouse can then be used to analyze the function of human or rat T2Rs, and to identify ligands for such T2Rs.

F. Modulators

The compounds tested as modulators of a T2R family member can be any small chemical compound, or a biological entity, such as a protein, sugar, nucleic acid or lipid. Alternatively, modulators can be genetically altered versions of a T2R family member. Typically, test compounds may be small chemical molecules and peptides. Essentially any chemical compound can be used as a potential modulator or ligand in the assays of the invention, although most often compounds can be dissolved in aqueous or organic (especially DMSO-based) solutions are used. The assays may be designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (articular chemical species or subclasses) that display a desired characteristic activity The compounds thus identified can serve as conventional "lead compounds" or can themselves be used as potential or actual consumer products.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.,* 37:487-93 (1991) and Houghton et al., *Nature,* 354:84-88 (1991)). Other chemistries for generating chemical diversity libraries can also be used. Such chemistries include, but are not limited to: peptoids (e.g., WO 91/19735), encoded peptides (e.g., WO 93/20242), random bio-oligomers (e.g., WO 92/00091), benzodiazepines (e.g., U.S. Pat. No. 5,288,514), diversomers such as hydantoins, benzodiazepines and dipeptides (Hobbs et al, *PNAS.,* 90:6909-13 (1993)), vinylogous polypeptides (Hagihara et al., *J. Amer. Chem. Soc.,* 114:6568 (1992)), nonpeptidal peptidomimetics with glucose scaffolding (Hirschmann et al. *J. Amer. Chem. Soc.,* 114:9217-18 (1992)), analogous organic syntheses of small compound libraries (Chen et al., *J. Amer. Chem. Soc.,* 116:2661 (1994)), oligocarbamates (Cho et al., *Science,* 261:1303 (1993)), peptidyl phosphonates (Campbell et al., *J. Org. Chem.,* 59:658 (1994)), nucleic acid libraries (Ausubel, Berger, and Sambrook, all supra), peptide nucleic acid libraries (U.S. Pat. No. 5,539,083), antibody libraries (Vaughn et al., *Nature Biotechnology,* 14(3):309-14 (1996) and PCT/US96/10287), carbohydrate libraries (Liang et al., *Science,* 274:1520-22 (1996) and U.S. Pat. No. 5,593,853), small organic molecule libraries (benzodiazepines, Baum, *C&EN,* January 18, page 33 (1993); thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS (Advanced Chem Tech, Louisville Ky.), Symphony (Rainin, Woburn, Mass.), 433A (Applied Biosystems, Foster City, Calif.), 9050 Plus (Millipore, Bedford, Mass.)). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences; Columbia, Md.; etc.).

In one aspect of the invention, the T2R modulators can be used in any food product, confectionery, pharmaceutical composition, or ingredient thereof to thereby modulate the taste of the product, composition, or ingredient in a desired manner. For instance, T2R modulators that enhance bitter taste sensation can be added to provide a bitter taste to a product or composition, while T2R modulators which block bitter taste sensations can be added to improve the taste of a product or composition.

G. Methods For Representing And Predicting The Perception Of Taste

The invention also preferably provides methods for representing the perception of taste and/or for predicting the perception of taste in a mammal, including in a human. Preferably, such methods may be performed by using the receptors and genes encoding said T2R proteins disclosed herein.

Also contemplated as within the invention, is a method of screening one or more compounds for the presence of a taste detectable by a mammal, comprising: contacting said one or more compounds with the disclosed receptors, preferably wherein the mammal is a human. Also contemplated as within the invention, is a method for representing taste perception of a particular taste in a mammal, comprising the steps of: providing values $X_1$ to $X_n$ representative of the quantitative stimulation of each of n taste receptors of said vertebrate, where n is greater than or equal to 4; and generating from said values a quantitative representation of taste perception. The taste receptors may be a taste receptor disclosed herein, the representation may constitutes a point or a volume in n-dimensional space, may constitutes a graph or a spectrum, and may constitutes a matrix of quantitative representations. Also, the providing step may comprise contacting a plurality of recombinantly-produced taste receptors with a test composition and quantitatively measuring the interaction of said composition with said receptors.

Also contemplated as within the invention, is a method for predicting the taste perception in a mammal generated by one or more molecules or combinations of molecules yielding unknown taste perception in a mammal, comprising the steps of: providing values $X_1$ to $X_n$ representative of the quantitative stimulation of each of n taste receptors of said vertebrate, where n is greater than or equal to 4, for one or more molecules or combinations of molecules yielding known taste perception in a mammal; and generating from said values a quantitative representation of taste perception in a mammal for the one or more molecules or combinations of molecules yielding known taste perception in a mammal, providing values $X_1$ to $X_n$ representative of the quantitative stimulation of each of n taste receptors of said vertebrate, where n is greater than or equal to 4, for one or more molecules or combinations of molecules yielding unknown taste perception in a mammal; and generating from said values a quantitative representation of taste perception in a mammal for the one or more molecules or combinations of molecules yielding unknown taste perception in a mammal, and predicting the taste perception in a mammal generated by one or more molecules or combinations of molecules yielding unknown taste perception in a mammal by comparing the quantitative representation of taste perception in a mammal for the one or more molecules or combinations of molecules yielding unknown taste perception in a mammal to the quantitative representation of taste perception in a mammal for the one or more molecules or combinations of molecules yielding known taste perception in a mammal. The taste receptors used in this method may include a taste receptor disclosed herein.

In another embodiment, novel molecules or combinations of molecules are generated which elicit a predetermined taste perception in a mammal by determining a value of taste perception in a mammal for a known molecule or combinations of molecules as described above; determining a value of taste perception in a mammal for one or more unknown molecules or combinations of molecules as described above; comparing the value of taste perception in a mammal for one or more unknown compositions to the value of taste perception in a mammal for one or more known compositions; selecting a molecule or combination of molecules that elicits a predetermined taste perception in a mammal; and combining two or more unknown molecules or combinations of molecules to form a molecule or combination of molecules that elicits a predetermined taste perception in a mammal. The combining step yields a single molecule or a combination of molecules that elicits a predetermined taste perception in a mammal.

In another embodiment of the invention, there is provided a method for simulating a taste, comprising the steps of: for each of a plurality of cloned taste receptors, preferably human receptors, ascertaining the extent to which the receptor interacts with the tastant; and combining a plurality of compounds, each having a previously-ascertained interaction with one or more of the receptors, in amounts that together provide a receptor-stimulation profile that mimics the profile for the tastant. Interaction of a tastant with a taste receptor can be determined using any of the binding or reporter assays described herein. The plurality of compounds may then be combined to form a mixture. If desired, one or more of the plurality of the compounds can be combined covalently. The combined compounds substantially stimulate at least 75%, 80%, or 90% of the receptors that are substantially stimulated by the tastant.

In another preferred embodiment of the invention, a plurality of standard compounds are tested against a plurality of taste receptors to ascertain the extent to which the receptors each interact with each standard compound, thereby generating a receptor stimulation profile for each standard compound. These receptor stimulation profiles may then be stored in a relational database on a data storage medium. The method may further comprise providing a desired receptor-stimulation profile for a taste; comparing the desired receptor stimulation profile to the relational database; and ascertaining one or more combinations of standard compounds that most closely match the desired receptor-stimulation profile. The method may further comprise combining standard compounds in one or more of the ascertained combinations to simulate the taste.

H. Kits

T2R genes and their homologs are useful tools for identifying taste receptor cells, for forensics and paternity determinations, and for examining taste transduction. T2R family member-specific reagents that specifically hybridize to T2R nucleic acids, such as T2R probes and primers, and T2R specific reagents that specifically bind to a T2R protein, e.g., T2R antibodies are used to examine taste cell expression and taste transduction regulation.

Nucleic acid assays for the presence of DNA and RNA for a T2R family member in a sample include numerous techniques are known to those skilled in the art, such as southern analysis, northern analysis, dot blots, RNase protection, S1 analysis, amplification techniques such as PCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques*, 4:230250 (1986); Haase et al., *Methods in Virology*, vol. VII, 189-226 (1984); and Names et al., eds., *Nucleic Acid Hybridization: A Practical Approach* (1987). In addition, a T2R protein can be detected with the various immunoassay techniques described above. The test sample is typically compared to both a positive control (e.g., a sample expressing a recombinant T2R protein) and a negative control.

The present invention also provides for kits for screening for modulators of T2R family members. Such kits can be prepared from readily available materials and reagents. For example, such kits can comprise any one or more of the following materials: T2R nucleic acids or proteins, reaction tubes, and instructions for testing T2R activity. Optionally, the kit contains a functional T2R polypeptide. A wide variety of kits and components can be prepared according to the present invention, depending upon the intended user of the kit and the particular needs of the user.

EXAMPLES

The following examples provide a summary of the isolated nucleic acid molecules of the invention, and polypeptide sequences corresponding to the conceptual translations of nucleic acid molecules. In the protein sequences presented herein, the one-letter code X or Xaa refers to any of the twenty common amino acid residues. In the DNA sequences presented herein, the one letter codes N or n refers to any of the of the four common nucleotide bases, A, T, C, or G.

hT2R51 Full-Length cDNA (BAC AC011654) (SEQ ID NO: 1)
hT2R51 Conceptual Translation (BAC AC011654) (SEQ ID NO: 2)
hT2R54 Full-Length cDNA (BAC AC024156) (SEQ ID NO: 3)
hT2R54 Conceptual Translation (BAC AC024156) (SEQ ID NO: 4)
hT2R55 Full-Length cDNA (BAC AC024156) (SEQ ID NO: 5)
hT2R55 Conceptual Translation (BAC AC024156) (SEQ ID NO: 6)
hT2R61 Full-Length cDNA (BAC AC018630) (SEQ ID NO: 7)
hT2R61 Conceptual Translation (BAC AC018630) (SEQ ID NO: 8)
hT2R63 Full-Length cDNA (BAC AC018630) (SEQ ID NO: 9)
hT2R63 Conceptual Translation (BAC AC018630) (SEQ ID NO: 10)
hT2R64 Full-Length cDNA (BAC AC018630) (SEQ ID NO: 11)
hT2R64 Conceptual Translation (BAC AC018630) (SEQ ID NO: 12)
hT2R65 Full-Length cDNA (BAC AC018630) (SEQ ID NO: 13)
hT2R65 Conceptual Translation (BAC AC018630) (SEQ ID NO: 14)

hT2R67 Full-Length cDNA (BAC AC018630) (SEQ ID NO: 15)
hT2R67 Conceptual Translation (BAC AC018630) (SEQ ID NO: 16)
hT2R71 Full-Length cDNA (BAC AC073264) (SEQ ID NO: 17)
hT2R71 Conceptual Translation (BAC AC073264) (SEQ ID NO: 18)
hT2R75 Full-Length cDNA (SEQ ID NO: 19)
hT2R75 Conceptual Translation (SEQ ID NO: 20)
hT2R59 Pseudogene (BAC AC018630) (SEQ ID NO: 21)
hT2R69 Pseudogene (BAC AC018630) (SEQ ID NO: 22)
mT2R33 Full-Length cDNA (BAC AC020619) (SEQ ID NO: 23)
mT2R33 Conceptual Translation (BAC AC020619) (SEQ ID NO: 24)

While the foregoing detailed description has described several embodiments of the present invention, it is to be understood that the above description is illustrative only and not limiting of the disclosed invention. The invention is to be limited only by the claims which follow.

What is claimed is:

1. An isolated nucleic acid encoding a G protein coupled receptor (GPCR) polypeptide involved in bitter taste transduction which polypeptide is at least 95% identical to the polypeptide of SEQ ID NO:4 or which encodes a polypeptide which is at least 95% identical to the entire extracellular or the transmembrane region of said GPCR polypeptide.

2. The isolated nucleic acid of claim 1 that encodes a polypeptide at least 96% identical to the polypeptide in SEQ ID NO:4 or to the entire extracellular or the transmembrane region of said GPCR polypeptide.

3. The isolated nucleic acid of claim 1 that encodes a polypeptide at least 97% identical to the polypeptide in SEQ ID NO:4 or to the entire extracellular or the transmembrane region of said GPCR polypeptide.

4. The isolated nucleic acid of claim 1 that encodes a polypeptide at least 96% identical to the polypeptide in SEQ ID NO:4 or to the entire extracellular or the transmembrane region of said GPCR polypeptide.

5. The isolated nucleic acid of claim 1 that encodes a polypeptide at least 98% identical to the polypeptide in SEQ ID NO:4 or to the entire extracellular or the transmembrane region of said GPCR polypeptide.

6. The isolated nucleic acid of claim 1 that encodes a polypeptide at least 99% identical to the polypeptide contained in SEQ ID NO:4 or to the entire extracellular or the transmembrane region of said GPCR polypeptide.

7. The isolated nucleic acid of claim 1 that encodes a polypeptide identical to the polypeptide contained in SEQ ID NO:4 or to the entire extracellular or the transmembrane region of said GPCR polypeptide.

8. The isolated nucleic acid of claim 1 which comprises the nucleic acid sequence contained in SEQ ID NO:3 or the entire extracellular or the transmembrane coding region of said GPCR polypeptide.

9. The isolated nucleic acid of claim 1 which is contained in a plasmid.

10. An isolated or recombinant cell containing a nucleic acid according to claim 1.

11. The isolated cell or recombinant cell of claim 10 which is selected from a bacterial, yeast, amphibian, mammalian and oocyte cell.

12. The isolated cell or recombinant cell of claim 10 which is a BHK, COS, HEK or CHO cell.

* * * * *